United States Patent [19]

Petrzilka et al.

[11] Patent Number: 4,550,981
[45] Date of Patent: Nov. 5, 1985

[54] LIQUID CRYSTALLINE ESTERS AND MIXTURES

[75] Inventors: Martin Petrzilka, Kaiseraugst; Martin Schadt, Seltisberg; Alois Villiger, Basel, all of Switzerland

[73] Assignee: Hoffmann-La Roche Inc., Nutley, N.J.

[21] Appl. No.: 530,830

[22] Filed: Sep. 9, 1983

[30] Foreign Application Priority Data

Sep. 30, 1982 [CH] Switzerland .................. 5757/82
Nov. 10, 1982 [CH] Switzerland .................. 6546/82
Jun. 27, 1983 [CH] Switzerland .................. 3499/83

[51] Int. Cl.[4] ............... G02F 1/13; C09K 3/34; C07C 121/52; C07C 54/70; C07C 69/90; C07C 79/26

[52] U.S. Cl. .................. 350/350 R; 252/299.63; 252/299.64; 252/299.65; 252/299.66; 252/299.67; 260/465 D; 260/465 H; 350/346; 560/1; 560/8; 560/59; 560/61; 560/62; 560/64; 560/65; 560/73; 560/102; 560/116; 560/118

[58] Field of Search ............ 252/299.63, 299.67, 252/299.66, 299.64, 299.65; 350/350 R, 350 S, 346; 560/59, 61, 64, 62, 102, 116, 118, 65, 73, 8, 1; 260/465 D, 465 H

[56] References Cited

U.S. PATENT DOCUMENTS

| | | |
|---|---|---|
| 3,915,883 | 10/1975 | Van Meter et al. ............ 252/299.64 |
| 3,947,375 | 3/1976 | Gray et al. .................. 252/299.66 |
| 4,001,137 | 1/1977 | Steinstrasser ................ 252/299.64 |
| 4,012,434 | 3/1977 | Steinstrasser ................ 252/299.5 |
| 4,113,647 | 9/1978 | Coates et al. ................ 252/299.63 |
| 4,119,558 | 10/1978 | Coates et al. ................ 252/299.62 |
| 4,229,015 | 10/1980 | Frause et al. ................ 252/299.63 |
| 4,341,652 | 7/1982 | Takei et al. ................. 252/299.67 |
| 4,368,135 | 1/1983 | Osman ........................ 252/299.63 |
| 4,405,488 | 9/1983 | Sugimori et al. .............. 252/299.63 |
| 4,406,814 | 9/1983 | Ferrato ...................... 252/299.62 |
| 4,410,283 | 10/1983 | DuBois et al. ................ 252/299.64 |
| 4,415,470 | 11/1983 | Eidenschink et al. ........... 252/299.63 |
| 4,438,268 | 3/1984 | Zaschke et al. ............... 252/299.61 |
| 4,460,770 | 7/1984 | Petrzilka et al. ............. 252/299.61 |
| 4,472,592 | 9/1984 | Takatsu et al. ............... 252/299.63 |
| 4,502,974 | 3/1985 | Sugimori et al. .............. 252/299.63 |
| 4,526,704 | 7/1985 | Petrzilka et al. ............. 252/299.61 |

FOREIGN PATENT DOCUMENTS

| | | |
|---|---|---|
| 19665 | 12/1980 | European Pat. Off. ....... 252/299.63 |
| 50023 | 4/1982 | European Pat. Off. ....... 252/299.63 |
| 56501 | 7/1982 | European Pat. Off. ....... 252/299.63 |
| 60646 | 9/1982 | European Pat. Off. ....... 252/299.63 |
| 84194 | 7/1983 | European Pat. Off. ....... 252/299.61 |
| 90671 | 10/1983 | European Pat. Off. ....... 252/299.63 |
| 2939782 | 4/1981 | Fed. Rep. of Germany ..... 252/299.64 |
| 3221462 | 1/1983 | Fed. Rep. of Germany ..... 252/299.63 |
| 3237367 | 4/1983 | Fed. Rep. of Germany ..... 252/299.63 |
| 3208089 | 9/1983 | Fed. Rep. of Germany ..... 252/299.63 |
| 3209178 | 9/1983 | Fed. Rep. of Germany ..... 252/299.63 |
| 3211601 | 10/1983 | Fed. Rep. of Germany ..... 252/299.63 |
| 3231707 | 3/1984 | Fed. Rep. of Germany ..... 252/299.63 |
| 55-84385 | 6/1980 | Japan ..................... 252/299.64 |
| 57-9742 | 1/1982 | Japan ..................... 252/299.63 |
| 57-7457 | 1/1982 | Japan ..................... 252/299.64 |
| 57-154158 | 9/1982 | Japan ..................... 252/299.63 |
| 58-13544 | 1/1983 | Japan ..................... 252/299.63 |
| 58-121247 | 7/1983 | Japan ..................... 252/299.63 |
| WO82/00654 | 3/1982 | PCT Int'l Appl. .......... 252/299.63 |
| 2078727A | 1/1982 | United Kingdom ........... 252/299.64 |
| 2085910 | 5/1982 | United Kingdom ........... 252/299.63 |
| 2098986 | 12/1982 | United Kingdom ........... 252/299.63 |

OTHER PUBLICATIONS

Osman, Maged A., et al., Mol. Cryst. Liq. Cryst., vol. 82, (Letters), pp. 331–338 (1983).

Kelker and Hatz, Handbook of Liquid Crystals, Verlag Chemie, 1980, pp. 84–85 & 644–671.

(List continued on next page.)

Primary Examiner—Teddy S. Gron
Attorney, Agent, or Firm—Jon S. Saxe; Bernard S. Leon; George W. Johnston

[57] ABSTRACT

Compounds of the formula

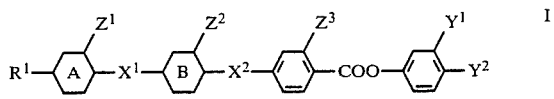

wherein $X^2$ is a single covalent bond or —COO—; $X^1$ is a single covalent bond, —COO—, —CH$_2$CH$_2$— or when $X^2$ is —COO—, $X^1$ also can be p—C$_6$H$_4$—, p—C$_6$H$_4$—CH$_2$CH$_2$—, —CH$_2$CH$_2$—p—C$_6$H$_4$, p—C$_6$H$_4$—COO— or —COO—p—C$_6$H$_4$; ring A is a benzene ring or trans-1,4-cyclohexylene; ring B is a benzene ring or when $X^2$ is —COO— and $X^1$ is a single covalent bond, —COO— or —CH$_2$CH$_2$—, ring B also can be trans-1,4-cyclohexylene; $Z^1$, $Z^2$ and $Z^3$ individually are hydrogen or when positioned on a benzene ring which is not linked directly with a further ring via a single covalent bond, $Z^1$, $Z^2$ and $Z^3$ also can be halogen, cyano or methyl; $Y^2$ is cyano, nitro, 2,2-dicyanovinyl or when $Y^1$ is hydrogen $Y^2$ also can be 2,2-dicyano-1-methylvinyl; $Y^1$ is halogen, cyano, C$_1$–C$_3$-alkyl or, when $X^1$ includes a benzene ring or —COO— or $Y^2$ is nitro or at least one of $Z^1$ and $Z^2$ is other than hydrogen, $Y^1$ also can be hydrogen; and $R^1$ is C$_1$–C$_{12}$-alkyl or when positioned on a benzene ring $R^1$ also can be C$_1$–C$_{12}$-alkoxy, their manufacture and use in liquid crystalline mixtures are described.

25 Claims, No Drawings

OTHER PUBLICATIONS

IBM Technical Disclosure Bull., vol. 17, No. 5, 1498–1501 (1974).
Research Disclosure Bull., 131, 28–31, (1975).
SID 79 Digest, 1979, 116–117.
Derwent 14410 E/08 [Japanese Kokai No. 82/5780(1/82)].
Derwent 14411 E/08 [Japanese Kokai No. 82/5781(1/82)].
Derwent 14412 E/08 [Japanese Kokai No. 82/5782(1/82)].
Derwent 14645 E/08 [Japanese Kokai No. 82/7457 (1/82)].
Appl. Phys. Lett. 41(8), 697 (1982) [Publ. Oct. 15, 1982].
Derwent 14413 E/08 [Japanese Kokai No. 82/5783 (1/82)].

LIQUID CRYSTALLINE ESTERS AND MIXTURES

BACKGROUND OF THE INVENTION

1. Field of the Invention

This invention relates to liquid crystalline compounds and mixtures.

2. Description

Liquid crystals have recently gained considerable importance as dielectrics in indicating devices, since the optical properties of such substances can be influenced by an applied voltage. Electro-optical devices based on liquid crystals are well known to the person skilled in the art and can be based on various effects such as, for example, dynamic scattering, the deformation of aligned phases (DAP type), the Schadt-Helfrich effect (rotation cell), the "guest-host effect" or a cholesteric-nematic phase transition.

The customary, static operation of liquid crystal indicating devices has in the past been replaced to an increasing extent by the so-called multiplex control. In this case there is mainly used an amplitude-selective multiplex procedure, whereby, however, by the procedures usually used in general only multiplex ratios of about 1:8 to 1:10 have been attained. In order to achieve higher multiplex rates in the control of liquid crystal displays, a two-frequency matrix addressing procedure has therefore been proposed (e.g. German Offenlegungsschriften Nos. 2 856 134 (Great Britain Pat. No. 2 013 014) and 2 907 940 (Great Britain Pat. No. 2 020 075).

In the case of this two-frequency procedure there is made use of the fact that the dielectric anisotropy of liquid crystals, which have upon application of a low-frequency voltage a positive anisotropy of the dielectric constants ($\Delta\epsilon=\epsilon_\parallel-\epsilon_\perp>0$, $\epsilon_\parallel$ signifying the dielectric constant along the longitudinal axis of the molecule and $\epsilon_\perp$ signifying the dielectric constant perpendicular thereto), is negative in the case of high frequencies. This effect has been ascribed to the hindering of the rotation of the long axis of the molecule round the short axis of the liquid crystal molecule [M. Schadt, Mol. Cryst. Liq. Cryst. 66 (1981) 319–336]. In contrast to $\epsilon_{81}$, in the case of $\epsilon_{195}$ dispersion effects only appear in the microwave range because of the barely hindered rotation of the molecule around its longitudinal axis. In the frequency range which is of interest here $\epsilon_\perp$ is therefore constant, while $\epsilon_\parallel$ and consequently also $\Delta\epsilon$ are frequency-dependent. The dielectric relaxation frequency, at which $\epsilon_\parallel=\epsilon_{195}$, is denoted in the technical terminology as the "cross-over frequency" ($f_c$). The most common nematic liquid crystals generally have cross-over frequencies of about 100 kHz and above at room temperature.

For the operation of an indicating device according to the two-frequency procedure there are used two alternating current sources, whereby the frequency of one of these sources must lie above the cross-over frequency and the frequency of the other source must lie below the cross-over frequency. Moreover, the voltage ratio of the signals for the on-condition and the off-condition must lie above a certain value. The greater this voltage ratio is, the more lines can be portrayed, i.e. the greater is the multiplex rate.

In addition, the two-frequency procedure offers the advantage that not only the switching-on process, but also the switching-off process can be influenced directly by the application of a corresponding alternating voltage, whereby an acceleration of the switching-off process is achieved. For example, in the case of a liquid crystal indicating element with a twisted nematic structure (rotation cell) the homogeneously orientated liquid crystal can be aligned in the field direction by the application of a voltage of low frequency ($f<f_c$) and can again be converted into the twisted, homogeneous orientation by the application of a voltage of high frequency ($f>f_c$).

Furthermore, with liquid crystal cells, which are based on guest-host effects [Applied Physics Letters 13 (1968) 91; J. Appl. Phys. 45 (1974) 4718 inter alia], there is possible with the use of liquid crystals with positive dielectric anisotropy in general only the reading of colourless image elements on a coloured background, since the colouring substances which are usable mainly exhibit positive dichroism. By homeotropic wall orientation and control according to the two-frequency procedure there can now also be produced with such liquid crystals coloured image elements (homogeneously orientated by the application of a voltage of high frequency) on a colourless background.

The two-frequency procedure has, however, the disadvantage that the energy consumption is high, since not only the amplitude of the applied alternating voltage, but also the frequency are high. In order to reduce the energy consumption, it is therefore important that the operating voltage can be maintained low. The cross-over frequency should for the same reason lie relatively low (thereby the capacitative losses are small).

SUMMARY OF THE INVENTION

The present invention concerns novel liquid crystalline compounds of the formula

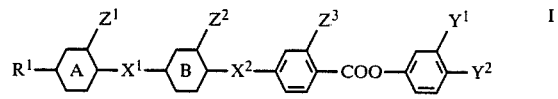

wherein $X^2$ signifies a single covalent bond or the ester group —COO—; $X^1$ signifies a single covalent bond, the ester group —COO—, the ethylene group —CH$_2$CH$_2$— or, insofar as $X^2$ signifies the ester group —COO—, also p—C$_6$H$_4$—, p—C$_6$H$_4$—CH$_2$CH$_2$—, —CH$_2$CH$_2$—p—C$_6$H$_4$—, p—C$_6$H$_4$—COO— or —COO—p—C$_6$H$_4$—; ring A signifies a benzene ring or trans-1,4-cyclohexylene; ring B signifies a benzene ring or, insofar as $X^2$ signifies the ester group —COO— and $X^1$ signifies a single covalent bond, the ester group —COO— or the ethylene group —CH$_2$CH$_2$—, also trans-1,4-cyclohexylene; $Z^1$, $Z^2$ and $Z^3$ signify hydrogen or on a benzene ring which is not linked directly with a further ring via a single covalent bond also halogen, cyano or methyl; $Y^2$ signifies cyano, nitro, 2,2-dicyanovinyl or, insofar as $Y^1$ signifies hydrogen, also 2,2-dicyano-1-methylvinyl; $Y^1$ signifies halogen, cyano, C$_1$-C$_3$-alkyl or, insofar as $X^1$ has a benzene ring or an ester group or $Y^2$ signifies nitro or $Z^1$ and/or $Z^2$ is different from hydrogen, also hydrogen; and $R^1$ signifies C$_1$-C$_{12}$-alkyl or on a benzene ring also C$_1$-C$_{12}$-alkoxy.

The invention is also concerned with the manufacture of the compounds of formula I above, their use for electro-optical purposes and liquid crystalline mixtures which contain compounds of formula I.

The inventive compounds of formula I have large mesophase ranges with high clearing points, the optically active compounds thereof (containing an asymmetric carbon atom in the side-chain $R^1$) generally exhibiting a cholesteric mesophase and the remaining compounds generally exhibiting a nematic mesophase. Moreover, the compounds in accordance with the invention are distinguished by large anisotropies of the dielectric constants and at the same time very low cross-over frequencies. Further, they have a good chemical and photochemical stability and in spite of the size of the molecule they have a remarkably good solubility in other liquid crystals.

The compounds in accordance with the invention can be used basically in any liquid crystalline mixtures, whereby on the basis of the above properties they are primarily suitable for increasing the dielectric anisotropies and the clearing points. However, the compounds in accordance with the invention are especially suitable as components of liquid crystalline dielectrics which are controlled according to the two-frequency procedure.

DETAILED DESCRIPTION OF THE INVENTION

The present invention concerns liquid crystalline tetracyclic and pentacyclic esters of the formula

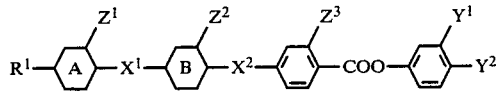

wherein $X^2$ is a single covalent bond or —COO—; $X^1$ is a single covalent bond, —COO—, —$CH_2CH_2$— or when $X^2$ is —COO—, $X^1$ also can be p—$C_6H_4$—, p—$C_6H_4$—$CH_2CH_2$—, —$CH_2CH_2$—p—$C_6H_4$, p—$C_6H_4$—COO— or —COO—p—$C_6H_4$; ring A is a benzene ring or trans-1,4-cyclohexylene; ring B is a benzene ring or when $X^2$ is —COO— and $X^1$ is a single covalent bond, —COO— or —$CH_2CH_2$—, ring B also can be trans-1,4-cyclohexylene; $Z^1$, $Z^2$ and $Z^3$ individually are hydrogen or when positioned on a benzene ring which is not linked directly with a further ring via a single covalent bond, $Z^1$, $Z^2$ and $Z^3$ also can be halogen, cyano or methyl; $Y^2$ is cyano, nitro, 2,2-dicyanovinyl or when $Y^1$ is hydrogen $Y^2$ also can be 2,2-dicyano-1-methylvinyl; $Y^1$ is halogen, cyano, $C_1$-$C_3$-alkyl or when $X^1$ includes a benzene ring or —COO— or $Y^2$ is nitro or at least one of $Z^1$ and $Z^2$ is other than hydrogen, $Y^1$ also can be hydrogen; and $R^1$ is $C_1$-$C_{12}$-alkyl or when positioned on a benzene ring $R^1$ also can be $C_1$-$C_{12}$-alkoxy.

It has now been found that the compounds of formula I have large mesophase ranges with high clearing points, the optically active compounds (containing an asymmetric carbon atom in the side-chain $R^1$) generally exhibiting a cholesteric mesophase and the remaining compounds generally exhibiting a nematic mesophase. Moreover, the compounds in accordance with the invention are distinguished by large anisotropies of the dielectric constants and at the same time very low cross-over frequencies. Further, they have a good chemical and photochemical stability and in spite of the size of the molecule they have a remarkably good solubility in other liquid crystals.

The compounds in accordance with the invention can be used basically in any liquid crystalline mixtures, whereby on the basis of the above properties they are primarily suitable for increasing the dielectric anisotropies and the clearing points. However, the compounds in accordance with the invention are especially suitable as components of liquid crystalline dielectrics which are controlled according to the two-frequency procedure.

As used herein, the term "benzene ring" denotes p-phenylene which is unsubstituted or if desired, has a lateral halogen, cyano or methyl substituent. p—$C_6H_4$— denotes p-phenylene.

The term "halogen" denotes fluorine, chlorine or bromine.

Unless otherwise stated, "alkyl" or "$C_1$-$C_{12}$-alkyl" denotes a straight-chain alkyl group of 1 to 12 carbon atoms or a branched-chain alkyl group of 1 to 12 carbon atoms. Exemplary straight-chain alkyl groups are methyl, ethyl, propyl, butyl, pentyl, hexyl, heptyl octyl, nonyl, decyl, undecyl and dodecyl. Exemplary branched-chain alkyl groups are isopropyl, isobutyl, isopentyl, isoheptyl, isooctyl, isononyl, isodecyl, isoundecyl, isododecyl, sec-butyl, 1-methylbutyl, 2-methylbutyl 3-methylphentyl, 4-methylhexyl and isopentyl. Lower alkyl denotes straight-chain and branched-chain alkyl groups of 1 to 5 carbon atoms. The term "$C_1$-$C_3$-alkyl" denotes methyl, ethyl, propyl and isopropyl.

The term "alkoxy" as well as any other groups in the specification containing "alkyl" denote moieties in which their "alkyl" portions are as defined previously. In particular, straight-chain alkoxy groups denote moieties having a straight-chain alkyl portion as previously defined. In particular, the term "$C_1$-$C_{12}$-alkoxy" embraces alkoxy groups in which the alkyl portion has the same significance as $C_1$-$C_{12}$-alkyl.

The term "alkali metal" denotes sodium, potassium or lithium.

The lateral groups $Z^1$, $Z^2$ and $Z^3$ signify hydrogen or, when they are attached to an "isolated" benzene ring, (i.e., to a p-phenylene ring which is not linked directly via a single covalent bond with a further ring (p-phenylene or trans-1,4-cyclohexylene), also halogen, cyano or methyl.

In formula I above ring B preferably signifies a benzene ring. Preferably $Z^1$, $Z^2$ and $Z^3$ signify hydrogen or at most two of $Z^1$, $Z^2$ and $Z^3$ (preferably $Z^2$ and/or $Z^3$) also signify chlorine. $X^1$ preferably signifies a single covalent bond, the ester group of —COO— or p-phenylene. $Y^1$ preferably signifies hydrogen, fluorine, chlorine, cyano or methyl, especially hydrogen, chlorine or cyano. $Y^2$ preferably signifies cyano or nitro. Those compounds in which $Y^1$ signifies chlorine and $Y^2$ signifies cyano or nitro are especially preferred. Compounds of formula I in which $Y^1$ signifies hydrogen and $Y^2$ signifies 2,2-dicyano-1-methylvinyl are also preferred. In general, ring A preferably signifies trans-1,4-cyclohexylene.

$R^1$ preferably signifies a straight-chain alkyl or alkoxy group or an isoalkyl or isoalkoxy group. The straight-chain alkyl and alkoxy groups, especially the straight-chain alkyl groups, are especially preferred groups denoted by $R^1$. $R^1$ preferably contains 3 to 10 and particularly 5 to 9 carbon atoms. Pentyl, hexyl and heptyl are particularly preferred groups denoted by $R^1$.

A preferred group of compounds of formula I comprises the compounds of the formula

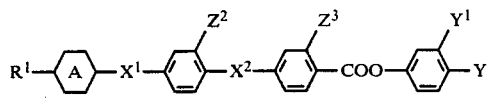

in which $X^2$ is a single covalent bond or —COO—; $Y^2$ is cyano, nitro, 2,2-dicyanovinyl or when $Y^1$ is hydrogen $Y^2$ also can be 2,2-dicyano-1-methylvinyl; $X^1$ is a single covalent bond, —COO— or when $X^2$ is —COO—, $X^1$ also can be p—$C_6H_4$—, p—$C_6H_4$—$CH_2CH_2$—, —$CH_2CH_2$—p—$C_6H_4$—, p—$C_6H_4$—COO— or —COO—p—$C_6H_4$—; ring A is p-phenylene or trans-1,4-cyclohexylene; $Z^2$ is hydrogen or when $X^1$ and $X^2$ are —COO—, $Z^2$ also can be chlorine; $Z^3$ is hydrogen or when $X^2$ is —COO—, $Z^3$ also can be chlorine; $Y^1$ is fluorine, chlorine, cyano, methyl or when $X^1$ includes a benzene ring or —COO— or $Y^2$ is nitro, $Y^1$ also can be hydrogen; and $R^1$ is $C_1$–$C_{12}$-alkyl or when positioned on a benzene ring $R^1$ also can be $C_1$–$C_{12}$-alkoxy.

$X^1$ in formula II preferably signifies a single covalent bond, the ester group —COO— or p-phenylene. Ring A preferably signifies trans-1,4-cyclohexylene and $Z^2$ preferably signifies hydrogen. Additionally, $X^2$ is —COO—; $Y^2$ is cyano or nitro; and $Z^3$ is hydrogen or chlorine.

Examples of preferred compounds in accordance with the invention are the compounds of formula II above in which $Z^2$ signifies hydrogen and $R^1$, ring A, $X^1$, $X^2$, $Z^3$, $Y^1$ and $Y^2$ have the significances given in Table 1 [$C_6H_4$ denotes p-phenylene, $C_6H_{10}$ denotes trans-1,4-cyclohexylene and a dash (—) denotes a single covalent bond] and the additional compounds of formula I named in the Examples hereinafter.

TABLE 1

| $R^1$ | Ring A | $X^1$ | $X^2$ | $Z^3$ | $Y^1$ | $Y^2$ |
|---|---|---|---|---|---|---|
| Pentyl | $C_6H_4$ | — | COO | H | CN | CN |
| Hexyl | $C_6H_4$ | — | COO | H | CN | CN |
| Heptyl | $C_6H_4$ | — | COO | H | CN | CN |
| Pentyl | $C_6H_{10}$ | — | COO | H | CN | CN |
| Hexyl | $C_6H_{10}$ | — | COO | H | CN | CN |
| Heptyl | $C_6H_{10}$ | — | COO | H | CN | CN |
| Heptyl | $C_6H_4$ | — | — | H | CN | CN |
| Heptyl | $C_6H_{10}$ | — | — | H | CN | CN |
| Pentyl | $C_6H_4$ | — | COO | Cl | CN | CN |
| Hexyl | $C_6H_4$ | — | COO | Cl | CN | CN |
| Heptyl | $C_6H_4$ | — | COO | Cl | CN | CN |
| Pentyl | $C_6H_{10}$ | — | COO | Cl | CN | CN |
| Hexyl | $C_6H_{10}$ | — | COO | Cl | CN | CN |
| Heptyl | $C_6H_{10}$ | — | COO | Cl | CN | CN |
| Heptyl | $C_6H_4$ | $C_6H_4$ | COO | H | CN | CN |
| Heptyl | $C_6H_{10}$ | $C_6H_4$ | COO | H | CN | CN |
| Heptyl | $C_6H_4$ | $C_6H_4$ | COO | Cl | CN | CN |
| Heptyl | $C_6H_{10}$ | $C_6H_4$ | COO | Cl | CN | CN |
| Pentyloxy | $C_6H_4$ | — | COO | H | CN | CN |
| Pentyloxy | $C_6H_4$ | — | — | H | CN | CN |
| Pentyloxy | $C_6H_4$ | — | COO | Cl | CN | CN |
| Pentyl | $C_6H_4$ | — | COO | H | Cl | CN |
| Hexyl | $C_6H_4$ | — | COO | H | Cl | CN |
| Heptyl | $C_6H_4$ | — | COO | H | Cl | CN |
| Pentyl | $C_6H_{10}$ | — | COO | H | Cl | CN |
| Hexyl | $C_6H_{10}$ | — | COO | H | Cl | CN |
| Heptyl | $C_6H_{10}$ | — | COO | H | Cl | CN |
| Heptyl | $C_6H_4$ | — | — | H | Cl | CN |
| Heptyl | $C_6H_{10}$ | — | — | H | Cl | CN |
| Pentyl | $C_6H_4$ | — | COO | Cl | Cl | CN |
| Hexyl | $C_6H_4$ | — | COO | Cl | Cl | CN |
| Heptyl | $C_6H_4$ | — | COO | Cl | Cl | CN |
| Pentyl | $C_6H_{10}$ | — | COO | Cl | Cl | CN |
| Hexyl | $C_6H_{10}$ | — | COO | Cl | Cl | CN |
| Heptyl | $C_6H_{10}$ | — | COO | Cl | Cl | CN |
| Heptyl | $C_6H_4$ | $C_6H_4$ | COO | H | Cl | CN |
| Heptyl | $C_6H_{10}$ | $C_6H_4$ | COO | H | Cl | CN |
| Heptyl | $C_6H_4$ | $C_6H_4$ | COO | Cl | Cl | CN |
| Heptyl | $C_6H_{10}$ | $C_6H_4$ | COO | Cl | Cl | CN |
| Pentyloxy | $C_6H_4$ | — | COO | H | Cl | CN |
| Pentyloxy | $C_6H_4$ | — | — | H | Cl | CN |
| Pentyloxy | $C_6H_4$ | — | COO | Cl | Cl | CN |
| Pentyl | $C_6H_4$ | — | COO | H | H | $NO_2$ |
| Hexyl | $C_6H_4$ | — | COO | H | H | $NO_2$ |
| Heptyl | $C_6H_4$ | — | COO | H | H | $NO_2$ |
| Pentyl | $C_6H_{10}$ | — | COO | H | H | $NO_2$ |
| Hexyl | $C_6H_{10}$ | — | COO | H | H | $NO_2$ |
| Heptyl | $C_6H_{10}$ | — | COO | H | H | $NO_2$ |
| Heptyl | $C_6H_4$ | — | — | H | H | $NO_2$ |
| Heptyl | $C_6H_{10}$ | — | — | H | H | $NO_2$ |
| Heptyl | $C_6H_4$ | — | COO | Cl | H | $NO_2$ |
| Heptyl | $C_6H_{10}$ | — | COO | Cl | H | $NO_2$ |
| Heptyl | $C_6H_4$ | — | COO | H | Cl | $NO_2$ |
| Heptyl | $C_6H_{10}$ | — | COO | H | Cl | $NO_2$ |
| Heptyl | $C_6H_4$ | — | — | H | Cl | $NO_2$ |
| Heptyl | $C_6H_{10}$ | — | — | H | Cl | $NO_2$ |
| Heptyl | $C_6H_4$ | — | COO | Cl | Cl | $NO_2$ |
| Heptyl | $C_6H_{10}$ | — | COO | Cl | Cl | $NO_2$ |
| Heptyl | $C_6H_4$ | $C_6H_4$ | COO | H | H | $NO_2$ |
| Heptyl | $C_6H_{10}$ | $C_6H_4$ | COO | H | H | $NO_2$ |
| Heptyl | $C_6H_4$ | $C_6H_4$ | COO | Cl | H | $NO_2$ |
| Heptyl | $C_6H_{10}$ | $C_6H_4$ | COO | Cl | H | $NO_2$ |
| Heptyl | $C_6H_4$ | $C_6H_4$ | COO | H | Cl | $NO_2$ |
| Heptyl | $C_6H_{10}$ | $C_6H_4$ | COO | H | Cl | $NO_2$ |
| Heptyl | $C_6H_4$ | $C_6H_4$ | COO | Cl | Cl | $NO_2$ |
| Heptyl | $C_6H_{10}$ | $C_6H_4$ | COO | Cl | Cl | $NO_2$ |
| Heptyl | $C_6H_4$ | $C_6H_4$ | COO | H | H | CN |
| Heptyl | $C_6H_{10}$ | $C_6H_4$ | COO | H | H | CN |
| Heptyl | $C_6H_4$ | $C_6H_4$ | COO | Cl | H | CN |
| Heptyl | $C_6H_{10}$ | $C_6H_4$ | COO | Cl | H | CN |
| Heptyl | $C_6H_4$ | — | COO | H | F | CN |
| Heptyl | $C_6H_4$ | — | COO | Cl | F | CN |
| Heptyl | $C_6H_4$ | — | COO | Cl | $CH_3$ | CN |
| Heptyl | $C_6H_4$ | — | — | H | F | CN |
| Heptyl | $C_6H_4$ | — | — | H | $CH_3$ | CN |
| Heptyl | $C_6H_4$ | $C_6H_4$ | COO | H | F | CN |
| Heptyl | $C_6H_4$ | $C_6H_4$ | COO | Cl | F | CN |
| Heptyl | $C_6H_4$ | $C_6H_4$ | COO | Cl | $CH_3$ | CN |
| Heptyl | $C_6H_4$ | — | COO | H | Cl | $CH=C(CN)_2$ |
| Heptyl | $C_6H_4$ | — | COO | Cl | Cl | $CH=C(CN)_2$ |
| Heptyl | $C_6H_4$ | — | — | H | Cl | $CH=C(CN)_2$ |
| Heptyl | $C_6H_4$ | $C_6H_4$ | COO | H | H | $CH=C(CN)_2$ |
| Heptyl | $C_6H_4$ | $C_6H_4$ | COO | Cl | Cl | $CH=C(CN)_2$ |
| Heptyl | $C_6H_{10}$ | $CH_2CH_2$—$C_6H_4$ | COO | Cl | Cl | CN |
| Heptyl | $C_6H_{10}$ | $CH_2CH_2$—$C_6H_4$ | COO | Cl | Cl | $NO_2$ |
| Heptyl | $C_6H_{10}$ | $CH_2CH_2$—$C_6H_4$ | COO | Cl | Cl | $CH=C(CN)_2$ |
| Heptyl | $C_6H_{10}$ | $CH_2CH_2$—$C_6H_4$ | COO | Cl | H | $C(CH_3)=C(CN)_2$ |
| Heptyl | $C_6H_{10}$ | $C_6H_4$—COO | COO | Cl | Cl | CN |
| Heptyl | $C_6H_{10}$ | $C_6H_4$—COO | COO | Cl | Cl | $NO_2$ |
| Heptyl | $C_6H_{10}$ | $C_6H_4$—COO | COO | Cl | Cl | $CH=C(CN)_2$ |
| Heptyl | $C_6H_{10}$ | $C_6H_4$—COO | COO | Cl | H | $C(CH_3)=C(CN)_2$ |

The compounds of formula I can be manufactured in accordance with the invention by esterifying an acid of the formula

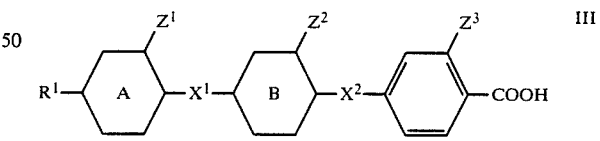

wherein $R^1$, A, B, $X^1$, $X^2$, $Z^1$, $Z^2$ and $Z^3$ have the significances given in formula I, or a reactive derivative thereof with a phenol of the formula

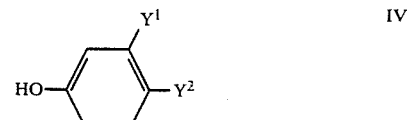

wherein $Y^1$ and $Y^2$ have the significance given in formula I, and, if desired, reacting a compound of formula I obtained in which $Z^1$, $Z^2$ or $Z^3$ signifies bromine with copper (I), cyanide, sodium cyanide or potassium cyanide.

The esterification of an acid of formula III or a reactive derivative thereof (e.g. the acid chloride or anhydride) with a phenol of formula IV can be carried out according to known methods. The reaction of the acid chloride (which is obtainable from the acid of the formula III, for example, by heating with thionyl chloride) with the phenol of formula IV is the preferred method. This reaction is conveniently carried out in an inert organic solvent such as, for example, diethyl ether, tetrahydrofuran, dimethylformamide, benzene, toluene, cyclohexane, carbon tetrachloride and the like. In order to bind the hydrogen chloride liberated in the reaction, there is conveniently used an acid-binding agent, for example tertiary amines, pyridines and the like. The acid-binding agent is preferably used in a large excess, so that it can simultaneously serve as the solvent. The temperature and pressure are not critical and the reaction is generally carried out at atmospheric pressure and a temperature between (about 23° C.) room temperature and the boiling point of the reaction mixture.

Although the compounds of formula I in which $Z^1$, $Z^2$ or $Z^3$ signifies cyano can be obtained in the manner described earlier, they are preferably manufactured by firstly preparing the corresponding bromo compound of formula I (as described above) and subsequently converting the bromo compound into the cyano compound in a known manner with copper (I) cyanide, sodium cyanide or potassium cyanide. This reaction is conveniently carried out in an inert organic solvent, for example in ethylene glycol, tetrahydrofurn, N-methylpyrrolidone, dimethylformamide, dimethyl sulphoxide, pyridine or acetonitrile. The reaction with copper (I) cyanide in dimethylformamide is preferred. The temperature and pressure at which this reaction is carried out are not critical. The reaction is conveniently carried out at atmospheric pressure and a temperature between room temperature and the boiling point of the reaction mixture.

The compounds of formula IV in which $Y^2$ signifies 2,2-dicyanovinyl can be prepared, for example, by converting 3-$Y^1$-anisole into 4-methoxy-2-$Y^1$-benzaldehyde by a Vilsmeier reaction with dimethylformamide in the presence of phosphorus oxychloride, then hydrolyzing the methoxy group (e.g. by heating under reflux with pyridinium chloride and subsequent fractional distillation) and subsequently converting the 4-hydroxy-2-$Y^1$-benzaldehyde obtained into the compound of formula IV in which $Y^2$ signifies 2,2-dicyanovinyl by Knoevenagel condensation with malononitrile (e.g. in the presence of catalytic amounts of glacial acetic acid and sodium acetate in boiling toluene). The remaining compounds of formula IV are known or can be prepared from known compounds by conventional techniques.

The compounds of formula III are likewise known or are analogues of known compounds and can be prepared according to known methods.

The compounds of formula III in which $X^2$ signifies the ester group —COO— can be prepared, for example, by esterifying a compound of the formula

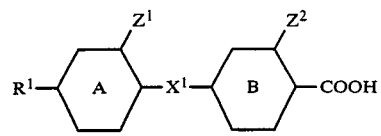

wherein $X^1$ signifies a single covalent bond, the ester group —COO—, the ethylene group —CH$_2$CH$_2$— or p—C$_6$H$_4$—, p—C$_6$H$_4$—CH$_2$CH$_2$—, —CH$_2$CH$_2$—p—C$_6$H$_4$, p—C$_6$H$_4$—COO— or —COO—p—C$_6$H$_4$ and $R^1$, A, B, $Z^1$ and $Z^2$ have the significances given in formula I, with 4-hydroxy-2-$Z^3$-benzaldehyde in methylene chloride in the presence of dicyclohexylcarbodiimide and 4-(dimethylamino)pyridine and converting the resulting aldehyde into the corresponding acid of formula III by Jones' oxidation with chromic acid and sulphuric acid.

In the preparation of the acids of formula III in which $X^1$ has an ethylene group —CH$_2$CH$_2$— and $X^2$ signifies a single covalent bond and of the acids of formula V in which $X^1$ has an ethylene group —CH$_2$CH$_2$—, the linkage of the rings is conveniently carried out by a Fouquet-Schlosser reaction or by a Wittig reaction. For example, 4-(bromoethyl)-2-$Z^2$-benzonitrile, 4'-(bromomethyl)-4-biphenylcarbonitrile, trans-4-(tosyloxymethyl)cyclohexanecarbonitrile and the like can be reacted with (4-$R^1$-2-$Z^1$-phenyl)methylmagnesium bromide, (trans-4-$R^1$-cyclohexyl)methylmagnesium bromide and the like in the presence of dilithium tetrachlorocuprate and the nitrile obtained can be hydrolyzed to the desired acid. Further, for example, 4-$R^1$-2-$Z^1$-benzaldehyde, trans-4-$R^1$-cyclohexanecarboxaldehyde etc can be reacted with (4-methoxycarbonyl-3-$Z^2$-phenyl)methyl-triphenylphosphonium bromide, (4'-methoxycarbonyl-4-biphenylyl)methyl-triphenylphosphonium bromide etc ($Z^1$ and $Z^2$ signifying hydrogen, fluorine, cyano or methyl) in the presence of a base (e.g. sodium methylate), then the double bond can be catalytically hydrogenated and finally the ester group can be saponified.

The starting materials required for these reactions are known or can be prepared according to known methods from known compounds. 4-alkoxy-2-$Z^1$-acetophenone can be converted by haloform degradation into 4-alkoxy-2-$Z^1$-benzoic acid and this can be converted into 4-alkoxy-1-(bromomethyl)-2-$Z^1$-benzene by reduction with lithium aluminium hydride and bromination (e.g. with tetrabromomethane and triphenylphosphine). From methyl 2,4-dimethylbenzoate there can be obtained, for example, by reaction with N-bromosuccinimide and subsequent isomer separation methyl 4-(bromomethyl)-2-methylbenzoate which can be converted into methyl 4-formyl-2-methylbenzoate in an analogous manner to Org. Synth. Coll. V, 825; the methyl 4-alkyl-2-methylbenzoate obtained after reaction with alkyl-triphenylphosphonium bromide and base and subsequent catalytic hydrogenation of the double bond can be saponified with sodium hydroxide to the acid or reduced with lithium aluminium hydride to the alcohol which finally can be converted with hydrogen bromide into the 4-alkyl-1-(bromomethyl)-2-methylbenzene or with manganese dioxide into the 4-alkyl-2-methylbenzaldehyde. 1-Alkyl-3-fluorobenzene can be converted, for example, into 4-alkyl-2-fluorobenzoic acid by reaction with butyl lithium and carbon dioxide and subsequent hydrolysis and 1-alkyl-3- chlorobenzene or 1-alkyl-3-bromobenzene can be converted into 4-alkyl-2-(chloro or bromo)benzoic acid by Friedel-Crafts acylation with acetyl chloride in the presence of aluminium trichloride and subsequent oxidation with sodium hypobromite; the acids obtained can then be converted with lithium aluminium hydride into the alcohols and these can be converted into the bromides with hydrogen bromide or into the aldehydes with manganese dioxide. Further, for example, 4-methyl-2-Z$^1$-benzoic acid can be reacted in sequence with thionyl chloride, ammonia and benzenesulphonyl chloride and the 4-methyl-2-Z$^1$-benzonitrile obtained can be converted into 4-(bromomethyl)-2-Z$^1$-benzonitrile with N-bromosuccinimide.

The compounds of formula I can be used in the form of mixtures with other liquid crystalline or non-liquid crystalline substances, such as, for example, with substances from the classes of Schiff's bases, azobenzenes, azoxybenzenes, phenylbenzoates, cyclohexanecarboxylic acid phenyl esters, cyclohexanecarboxylic acid cyclohexyl esters, cinnamic acid derivatives, biphenyls, terphenyls, phenylcyclohexanes, cyclohexylbiphenyls, phenylpyrimidines, diphenylpyrimidines, cyclohexylphenylpyrimidines, phenyldioxans, 2-cyclohexyl-1-phenylethanes and the like. Such substances are known to the person skilled in the art and many of them are, moreover, commercially available.

However, the compounds in accordance with the invention are preferably used as components of liquid crystalline dielectrics which are controlled according to the two-frequency procedure. These liquid crystalline mixtures preferably comprise three components A, B and C, each of which contains one or more compounds, with component A having a viscosity of at most about 40 cp, a clearing point of at least about 40° C. and a dielectric anisotropy between about −2 and about +1, component B having a dielectric anisotropy below about −2, component C having a dielectric anisotropy above about +10, a clearing point of at least about 100° C. and a cross-over frequency in the total mixture of at most about 15 kHz at 20° C., and component C containing at least one compound of formula I.

Such mixtures preferably have at least about 30 wt.% of component A, about 3–50 wt.% of component B and about 5–40 wt.% of component C and particularly of about 30–87 wt.% of component A, about 3–40 wt.% of component B and about 10–30 wt.% of component C. The amount of compounds of formula I in the total mixture conveniently amounts to at least about 1 wt.% and preferably at least about 5 wt.%.

Compounds and mixtures having the above properties required for the components A, B and C are basically known to the person skilled in the art. The total mixture must have nematic or cholesteric properties. Component A can be nematic or cholesteric and component C can be nematic, cholesteric or, as long as the total mixture is not smectic, also smectic. Components A and C must have at least monotropic liquid crystalline properties. However, there are preferred those mixtures in which at least component C is enantiotropic liquid crystalline and there are especially preferred those mixtures in which components A and C are enantiotropic liquid crystalline. Individual compounds in the mixtures in accordance with the invention and component B can, however, be liquid crystalline or non-liquid crystalline, but in the latter case care should be taken that the mesophase range of the total mixture is not restricted too severely.

Compounds and mixtures which are suitable as component A are to a large extent known and many of them are also commercially available. The following compounds or their mixtures are especially suitable:

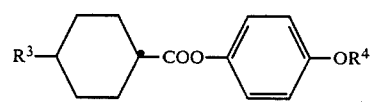 VI

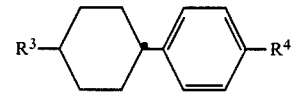 VII

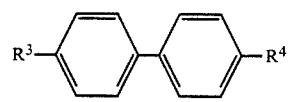 VIII

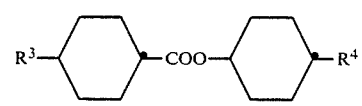 IX

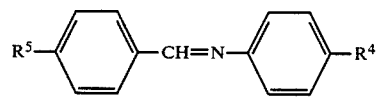 X

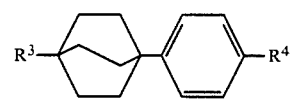 XI

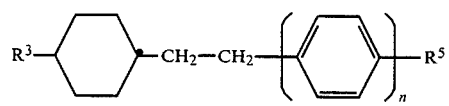 XII

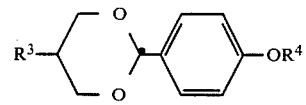 XIII

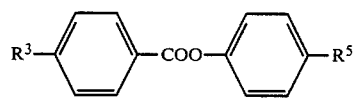 XIV

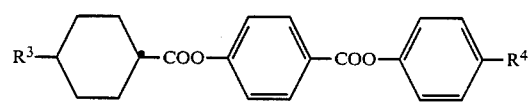 XV

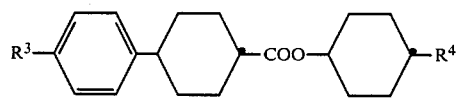 XVI

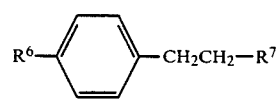 XVII

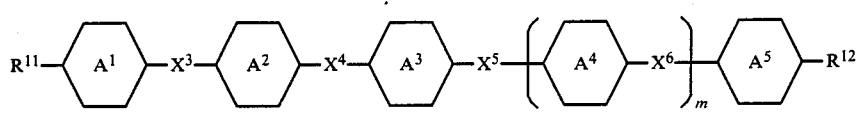

wherein $R^3$ and $R^4$ signify straight-chain alkyl groups containing 1 to 8 carbon atoms, $R^5$ signifies a straight-chain alkyl or alkoxy group containing 1 to 8 carbon atoms and n is 1 or 2; $R^6$ signifies trans-4-alkylcyclohexyl, 4'-alkyl-4-biphenylyl, p-(trans-4-alkylcyclohexyl)phenyl, 2-(trans-4-alkylcyclohexyl)ethyl or p-[2-(trans-4-alkylcyclohexyl)ethyl]phenyl and $R^7$ signifies trans-4-alkylcyclohexyl, or $R^6$ signifies trans-4-alkylcyclohexyl and $R^7$ signifies p-(trans-4-alkylcyclohexyl)phenyl, p-[2-(trans-4-alkylcyclohexyl)ethyl]phenyl or 4'-(trans-4-alkylcyclohexyl)-4-biphenylyl, or $R^6$ signifies p-alkylphenyl and $R^7$ signifies p-[2-(trans-4-alkylcyclohexyl)ethyl]phenyl, and the alkyl groups in $R^6$ and $R^7$ are straight-chain groups containing 1 to 7 carbon atoms; m signifies the number 0 or 1; one of the symbols $X^3$ and $X^4$ signifies an ester group —COO— or —OOC— and the remainder of the symbols $X^3$, $X^4$, $X^5$ and $X^6$ signify a single covalent bond or one of these symbols also signifies the ethylene group —CH$_2$CH$_2$—; rings $A^1$ and $A^5$ signify a group of the formula

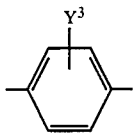

or trans-1,4-cyclohexylene; rings $A^2$, $A^3$ and $A^4$ signify a group of formula XIX or, provided that they are not linked with at least one of the other two of these rings by a single covalent bond, also trans-1,4-cyclohexylene; $Y^3$ signifies hydrogen or on one of the rings of formula XIX which is not linked with a further ring via a single covalent bond also fluorine, chlorine or methyl and $R^{11}$ and $R^{12}$ signify straight-chain alkyl containing 1 to 7 carbon atoms or on a ring of formula XIX also straight-chain alkoxy containing 1 to 7 carbon atoms. The compounds of formulae VII, IX and XV–XVIII are especially preferred and the compounds of formula VI are particularly preferred.

Compounds which are suitable for or as component B are, for example, pyridazine derivatives such as, for example, the phenyl pyridazines and diphenylpyridazines mentioned in Z. Chemie 17, 333 (1977), J. prakt. Chemie 151, 221 (1938), Z. Chemie 6, 467 (1966) and Mol. Cryst. Liq. Cryst. 25, 299 (1974), and especially the compounds which are described in German Offenlegungsschriften Nos. 2 933 563 and 2 937 700 which have two lateral cyano groups on a benzene ring. Especially preferred compounds are the dicyanophenyl esters of the formula

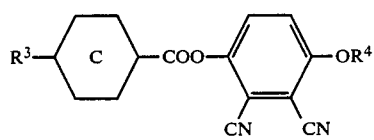

wherein $R^3$ and $R^4$ signify straight-chain alkyl groups containing 1 to 8 carbon atoms and ring C denotes p-phenylene or a trans-1,4-disubstituted cyclohexane ring, the dicyanobenzenes of the formula

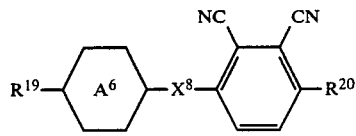

wherein $R^{19}$ and $R^{20}$ signify straight-chain $C_1$–$C_{12}$-alkyl or when positioned on a benzene ring also straight-chain $C_1$–$C_{12}$-alkoxy or one of $R^{19}$ and $R^{20}$ also signifies a group of the formula

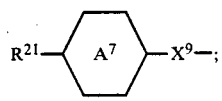

$X^8$ and $X^9$ signify single covalent bonds or one of $X^8$ and $X^9$ also signifies an ethylene group —CH$_2$CH$_2$—; rings $A^6$ and $A^7$ signify 1,4-phenylene or, insofar as $X^8$ or $X^9$ signifies an ethylene group —CH$_2$CH$_2$—, also trans-1,4-cyclohexylene; and $R^{21}$ signifies straight-chain $C_1$–$C_{12}$-alkyl or on a benzene ring $A^7$ also straight-chain $C_1$–$C_{12}$-alkoxy, and the cyclohexylpyridazines of the formula

XXI wherein $R^8$ signifies a straight-chain alkyl group containing 1 to 12 carbon atoms, $R^9$ signifies an alkyl, alkoxy, p-alkylphenyl, p-alkoxyphenyl or trans-4-alkylcyclohexyl group and the alkyl and alkoxy groups in $R^9$ are straight-chain groups containing 1 to 10 carbon atoms. Under the aforementioned "dielectric anisotropy" of component B there is to be understood in the case of non-liquid crystalline components the extrapolated value (from liquid crystalline mixtures which contain this component) of the dielectric anisotropy at a temperature which lies 10° C. below the extrapolated (virtual) clearing point. For example, the aforementioned pyridazines have dielectric anisotropies of about $-9$.

For or as component C there are suitable, for example, compounds containing 3 or 4 p-phenylene or trans-1,4-cyclohexylene groups, a polar end group and optionally a lateral halogen or cyano substituent. Such compounds are partly known and are described, for example, in Mol. Cryst. Liq. Cryst. 63, 129 (1981) and German Offenlegungsschriften Nos. 2 736 772 (U.S. Pat. No. 4,149,413), 2 752 975 (U.S. Pat. No. 4,293,434), and 3 046 872 (U.S. Pat. No. 4,363,767).

The compounds of formula I above and especially the compounds of formula I which are named as being preferred have now been found to be especially suitable compounds for component C. These compounds have large nematic or cholesteric mesophases with high clearing points, a good solubility and cross-over frequencies which generally lie distinctly below 10 kHz. Further, at frequencies below the cross-over frequency they have a large positive dielectric anisotropy and at frequencies above the cross-over frequency they have a large negative dielectric anisotropy. These properties make possible especially high multiplex rates and a low energy consumption in the operation of indicating devices according to the two-frequency procedure.

In addition to the compounds of formula I there are especially suitable for component C also compounds of the formula

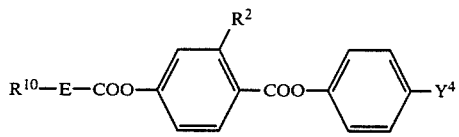

XXII wherein $R^2$ signifies hydrogen, fluorine, chlorine, bromine or the cyano group, $Y^4$ signifies 2,2-dicyanovinyl, 2,2-dicyano-1-methylvinyl or cyano, $R^{10}$ and E together signify p-$R^{10}$-phenyl, trans-4-$R^{10}$-cyclohexyl, 4'-$R^{10}$-4-biphenylyl, p-(trans-4-$R^{10}$-cyclohexyl)phenyl, p-(5-$R^{10}$-2-pyrimidinyl)phenyl, p-[2-(p'-$R^{10}$-phenyl)ethyl]phenyl, p-[2-(trans-4-$R^{10}$-cyclohexyl)ethyl]phenyl, trans-4-[2-(p-$R^{10}$-phenyl)ethyl]cyclohexyl or trans-4-[2-(trans-4-$R^{10}$-cyclohexyl)ethyl]cyclohexyl and $R^{10}$ signifies a straight-chain alkyl group containing 1 to 12 carbon atoms or when positioned on a benzene ring also a straight-chain alkoxy group containing 1 to 12 carbon atoms. These compounds also have a large nematic mesophase range, low cross-over frequencies and large absolute dielectric anisotropies.

Mixtures in accordance with the invention with cross-over frequencies of at most about 10 kHz at 20° C. are preferred and those with cross-over frequencies of at most about 5 kHz are especially preferred.

The mixtures in accordance with the invention can also contain (depending on properties as constituents of components A, B and C) optically active compounds, for example optically active biphenyls, and/or dichroic colouring substances, for example azo, azoxy or anthraquinone colouring substances. The amount of such compounds is determined by the solubility, the desired pitch, colour, extinction and the like. Preferably, the amount of optically active compounds amounts to at most about 4 wt.% and the amount of dichroic colouring substance amounts to at most about 10 wt.%, these percentages being based on the total mixture.

The manufacture of the liquid crystalline mixtures in accordance with the invention can be carried out in a known manner; for example, by heating a mixture of the constituents to a temperature barely above the clearing point and subsequently cooling said mixture.

The production of an electro-optical device containing a mixture in accordance with the invention can also be carried out in a known manner; for example, by evacuating a suitable cell and introducing the mixture into the evacuated cell.

The compounds of formula XVII are novel. They can be prepared as illustrated by the following Reaction Schemes 1 and 2 in which $R^{15}$ signifies trans-4-alkylcyclohexyl, 4'-alkyl-4-biphenylyl, p-(trans-4-alkylcyclohexyl)phenyl or 2-(trans-4-alkylcyclohexyl)ethyl and $R^{16}$ signifies trans-4-alkylcyclohexyl or $R^{15}$ signifies trans-4-alkylcyclohexyl and $R^{16}$ signifies p-(trans-4-alkylcyclohexyl)phenyl, p-[2-(trans-4-alkylcyclohexyl)ethyl]phenyl or 4'-(trans-4-alkylcyclohexyl)-4-biphenylyl or $R^{15}$ signifies p-alkylphenyl and $R^{16}$ signifies p-[2-(trans-4-alkylcyclohexyl)ethyl]phenyl and $R^{13}$, $R^{14}$ and the alkyl groups in $R^{15}$ and $R^{16}$ are straight-chain alkyl groups containing 1 to 7 carbon atoms.

Scheme 1

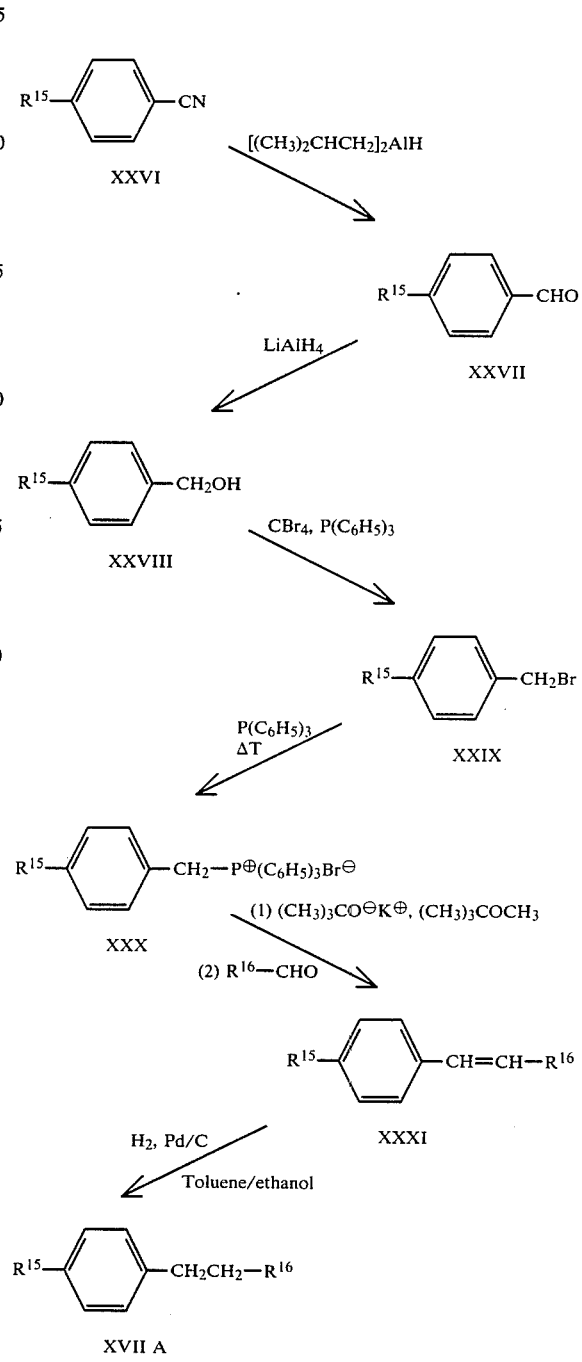

Scheme 2

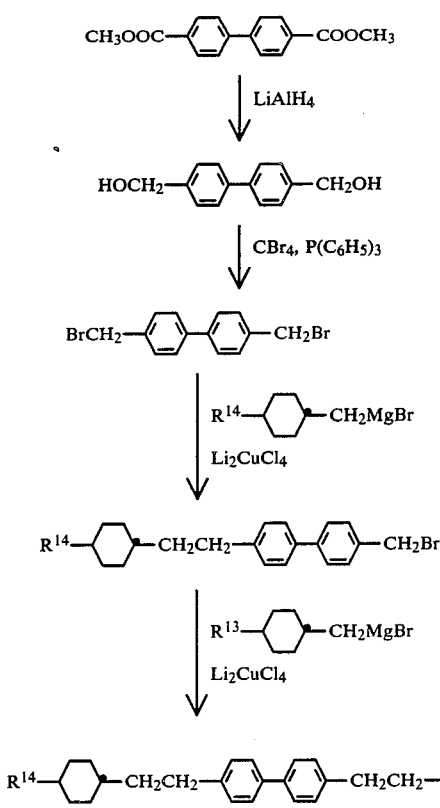

The compounds of formula R$^{16}$-CHO in Scheme 1 can be obtained in a simple and conventional manner from known compounds; for example, the trans-4-alkyl-cyclohexanecarboxaldehydes can be obtained by Rosenmund reduction of the corresponding acid chlorides and the remaining compounds can be obtained by reducing the corresponding cyano compounds.

By reacting the compound of formula XXXIV with Grignard reagents in accordance with Scheme 2 there can be obtained compounds of formula XXXV or directly compounds of formula XVIIB in which R$^{13}$ and R$^{14}$ have the same significance. When at least about 2 mol of Grignard reagent are used per mol of the compound of formula XXXIV there is generally predominantly formed directly a compound of formula XVIIB.

The esters of formula XVIII are also novel. They can be obtained according to esterification known methods (e.g. in an analogous manner to the manufacture of the compounds of formula I). The starting materials required for the preparation of the esters of formula XVIII known or are analogues of known compounds and can be prepared according to known methods.

The compounds of formula LVII are also novel. They can be prepared in a known manner in that (a) for the preparation of the compounds of formula LVII in which R$^{20}$ signifies straight-chain C$_1$-C$_{12}$-alkyl or a group of formula LVIII, a compound of the formula

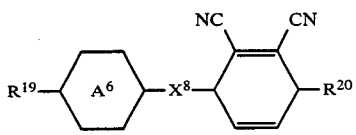

wherein R$^{20}$ signifies straight-chain C$_1$-C$_{12}$-alkyl or a group of formula LVIII and R$^{19}$, X$^8$ and ring A$^6$ have the significances given above, is oxidized (e.g. with 2,3-dichloro-5,6-dicyano-p-benzoquinone in dioxan or by catalytic dehydrogenation in the presence of a palladium catalyst), or (b) for the preparation of the compounds of formula LVII in which R$^{20}$ signifies straight-chain C$_1$-C$_{12}$-alkyl or a group of formula LVIII, hydrogen cyanide is cleaved off (e.g. with caesium fluoride in dimethylformamide) from a compound of the formula

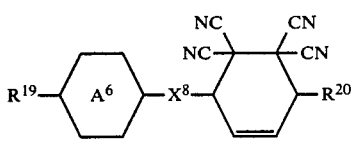

wherein R$^{20}$ signifies straight-chain C$_1$-C$_{12}$-alkyl or a group of formula LVIII and R$^{19}$, X$^8$ and ring A$^6$ have the significances given above, or (c) for the preparation of the compounds of formula LVII in which R$^{20}$ signifies straight-chain C$_1$-C$_{12}$-alkoxy, a compound of the formula

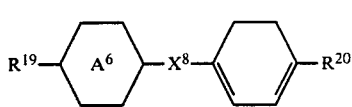

wherein R$^{20}$ signifies straight-chain C$_1$-C$_{12}$-alkoxy and R$^{19}$, X$^8$ and ring A$^6$ have the significances given above, is reacted with dicyanoacetylene (Diels-Alder reaction, for example in tetrahydrofuran) and ethylene is subsequently cleaved off (e.g. by heating).

The compounds of formula LIX can be obtained, for example, by reacting an aldehyde of the formula

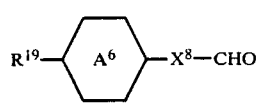

with a phosphonium salt of the general formula

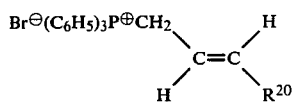

wherein R$^{19}$, R$^{20}$, X$^8$ and ring A$^6$ have the significances given in formula LIX, in diethyl ether in the presence of butyl lithium and converting the diene obtained into a compound of formula LIX by Diels-Alder reaction with dicyanoacetylene in tetrahydrofuran. The compounds of formula LXIII and the compounds of formula LXII in which X$^8$ signifies a single covalent bond are known or are analogues of known compounds which can be prepared by conventional techniques. The

Scheme 4
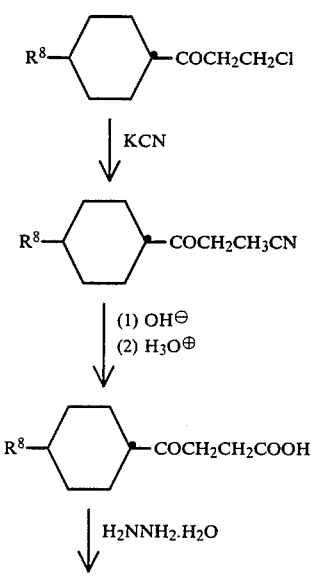
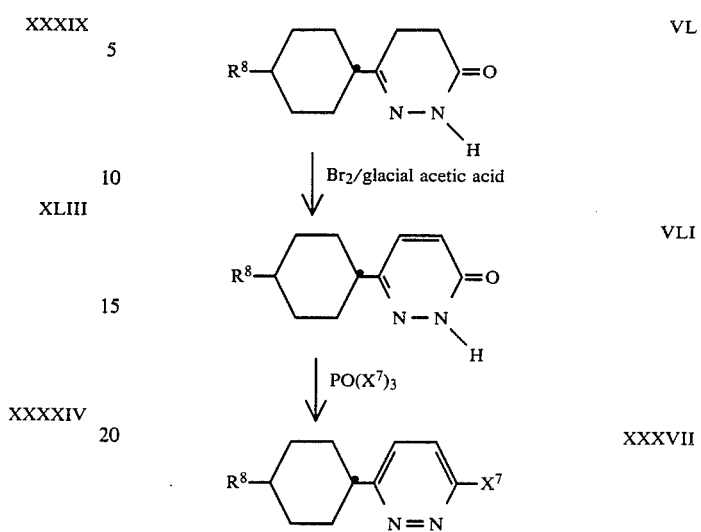
Scheme 5
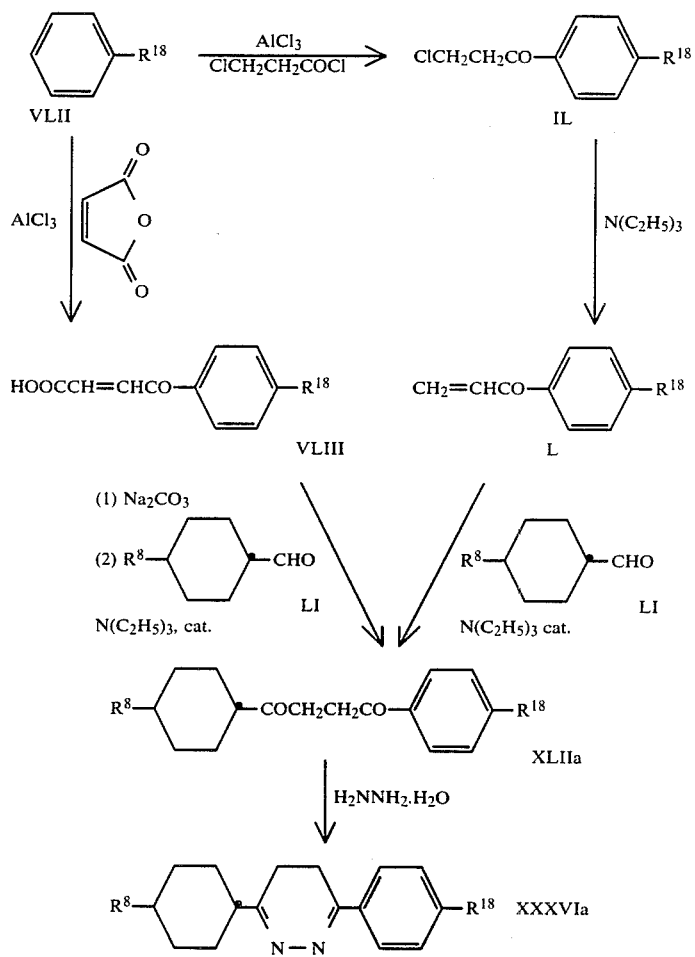

compounds of formula LXII in which $X^8$ signifies an ethylene group can be obtained, for example, by heating a corresponding compound of formula LXII in which $X^8$ signifies a single covalent bond with $(C_6H_5)_3P=CH-COOC_2H_5$ to reflux in benzene, catalytically hydrogenating the resulting $\alpha,\beta$-unsaturated ester in ethanol in the presence of a palladium catalyst, reducing the ester obtained with lithium aluminium hydride in diethyl ether and oxidizing the alcohol obtained to the desired aldehyde with pyridinium chlorochromate in methylene chloride.

The compounds of formula LX can be prepared, for example, by reacting an aldehyde of formula LXII with a phosphonium salt of formula LXIII in absolute diethyl ether in the presence of butyl lithium and converting the diene obtained into a compound of formula LX by Diels-Alder reaction with tetracyanoethylene in diethyl ether.

The compounds of formula LXI can be prepared, for example, by reducing a compound of the formula

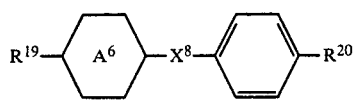

LXIV wherein $R^{20}$ signifies straight-chain $C_1$–$C_{12}$-alkoxy and $R^{19}$, $X^8$ and ring $A^6$ have the significances given in formula LVII, with lithium and liquid ammonia (preferably in a diethyl ether/ethanol mixture). There is generally obtained the 1,4-diene or a mixture of the 1,3-diene (a compound of formula LXI) and the 1,4-diene. The isomerization to the 1,3-diene can be carried out, for example, using 2,3-dichloromaleic anhydride. This is preferably carried out by using the product obtained in the above reduction directly for the subsequent Diels-Alder reaction [variant (c)] and adding 2,3-dichloromaleic anhydride to the reaction mixture.

The compounds of formula XXI are also novel. They can be prepared in a known manner in that (a) for the preparation of the compounds of formula XXI in which $R^9$ signifies an alkyl, p-alkylphenyl, p-alkoxyphenyl or trans-4-alkylcyclohexyl group, a compound of the formula

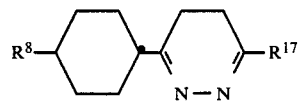

XXXVI wherein $R^{17}$ signifies an alkyl, p-alkylphenyl, p-alkoxyphenyl or trans-4-alkylcyclohexyl group, the alkyl and alkoxy groups in $R^{17}$ are straight-chain groups containing 1 to 10 carbon atoms, and $R^8$ has the above significance, or a tautomeric dihydropyridazine is oxidized (e.g. with 2,3-dichloro-5,6-dicyano-p-benzoquinone in dioxan, with sodium nitrite in glacial acetic acid and ethanol, with isopentyl nitrite in glacial acetic acid or preferably by catalytic dehydrogenation with palladium, platinum and the like), or (b) for the preparation of the compounds of formula XXI in which $R^9$ signifies an alkoxy group, a compound of the formula

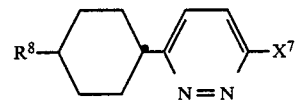

XXXVII wherein $X^7$ signifies chlorine or bromine and $R^8$ has the above significance, is reacted with an alkali metal alcoholate (e.g. sodium methylate).

The compounds of formula XXXVI can rearrange to tautomeric compounds by migration of the double bonds in the dihydropyridazine ring. Such rearrangements can be brought about, for example, by the presence of a trace of acid or base. Since the tautomeric dihydropyridazines can, however, also be oxidized under the above conditions to compounds of formula XXI, not only a compound of formula XXXVI but also a tautomeric dihydropyridazine or a mixture of such compounds can be reacted in accordance with variant (a).

The starting materials of formulae XXXVI and XXXVII are novel. They can be prepared as illustrated in the following Reaction Schemes 3-6 in which $R^8$, $R^{17}$ and $X^7$ have the above significances and $R^{18}$ signifies a straight-chain alkyl or alkoxy group containing 1 to 10 carbon atoms.

Scheme 3

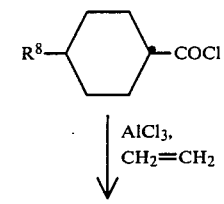

XXXVIII

AlCl$_3$,
CH$_2$=CH$_2$

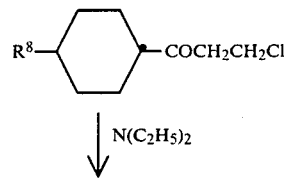

XXXIX

N(C$_2$H$_5$)$_2$

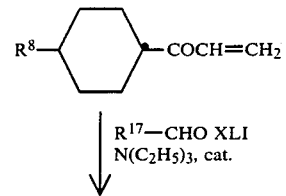

XL $R^{17}$—CHO XLI
N(C$_2$H$_5$)$_3$, cat.

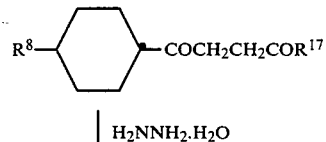

XLII

H$_2$NNH$_2$·H$_2$O

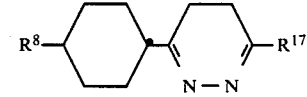

XXXVI

Scheme 6

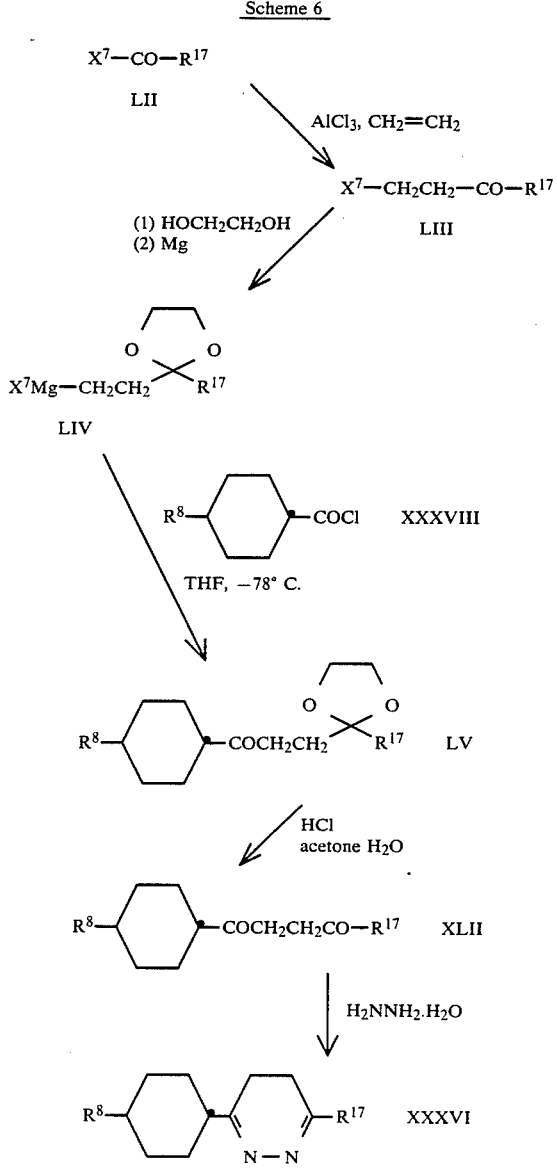

The starting materials of formulae XXXVIII, XLI, VLII, LI and LII are known or are analogues of known compounds and can be prepared in a known manner. For example, the aldehydes of formula LI can be prepared by Rosenmund reduction of the acid chlorides of formula XXXVIII.

The addition of an aldehyde to a compound of formula XL, VLIII or L can be carried out according to the method of Stetter [Chem. Ber. 114 (1981) 581] in the presence of a 1,3-thiazolium salt catalyst. 3-Benzyl-5-(2-hydroxyethyl)-4-methyl-1,3-thiazolium chloride is the preferred catalyst for the addition of an aldehyde of formula LI or of an aldehyde of formula XLI in which $R^{17}$ signifies alkyl or trans-4-alkylcyclohexyl and 3,4-dimethyl-5-(2-hydroxyethyl)-1,3-thiazolium iodide is the preferred catalyst for the addition of an aldehyde of formula XLI in which $R^{17}$ signifies p-alkylphenyl or p-alkoxyphenyl.

The coupling of a compound of formula LIV with a compound of formula XXXVIII can be carried out according to the method described by T. Sato et al., Bull. Chem. Soc. Japan 54 (1981) 505.

As mentioned above, the compounds of formula XXXVI can also exist in tautomeric form or as a mixture of tautomeric forms.

The compounds of formula XXII are in part novel compounds. They can be prepared by esterification in an analogous manner to the compounds of formula I. The acids required for the preparation of the compounds of formula XXII can be obtained as illustrated in Reaction Scheme 7 in which $R^2$, $R^{10}$ and E have the significances given in formula XXII above:

Scheme 7

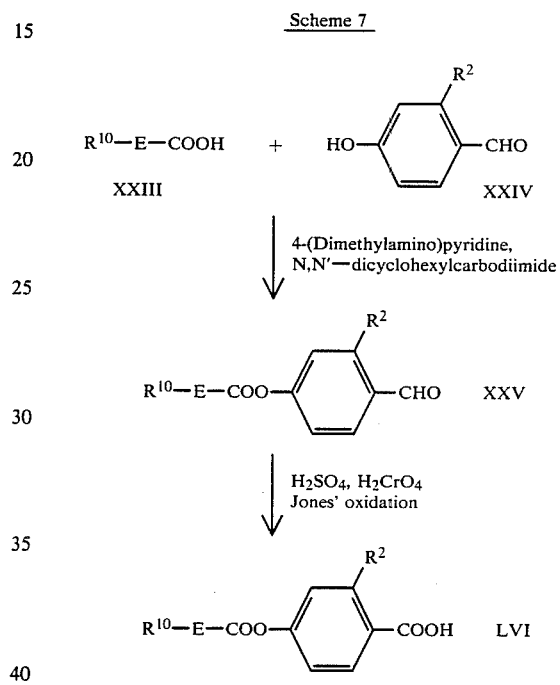

The compounds of formulae XXIII and XXIV are known or can be prepared according to known methods from known compounds.

The invention is also concerned with all novel compounds, mixtures, processes, uses and devices as herein described.

In the following Mixture Examples and chemical Examples, C denotes a crystalline phase, S denotes a smectic phase, N denotes a nematic phase, Ch denotes a cholesteric phase and I signifies the isotropic phase. $f_c$ denotes the cross-over frequency, $\Delta\epsilon_l$ denotes the low-frequency ("static") dielectric anisotropy (measured at frequencies which lie distinctly below the cross-over frequency), $\Delta\epsilon_h$ denotes the high-frequency dielectric anisotropy (measured at frequencies which lie distinctly above the cross-over frequency) and $\eta$ denotes the viscosity (bulk viscosity). Unless otherwise stated, percentages and ratios relating to solvent mixtures are expressed in volume, purity data determined by gas chromatography are expressed in area % and the remaining percentages and ratios are expressed in weight, temperatures are in degrees Celsius (°C.), normal pressure is about 1 atmosphere and room temperature is about 23° C. The petroleum ether is a well-known mixture of low-boiling hydrocarbons. Unless indicated otherwise, the mixture and chemical examples were carried out as written.

The following Mixture Examples are examples of preferred mixtures in accordance with the invention which are suitable for the control according to the two-frequency procedure. The relationship of the individual constituents of the total mixtures to the components A, B and C will be evident from the above details.

Mixture Example 1
- 11.4 wt. % of trans-4-butylcyclohexanecarboxylic acid p-ethoxyphenyl ester,
- 16.0 wt. % of trans-4-butylcyclohexanecarboxylic acid p-pentyloxyphenyl ester,
- 10.3 wt. % of trans-4-pentylcyclohexanecarboxylic acid p-methoxyphenyl ester,
- 12.4 wt. % of trans-4-pentylcyclohexanecarboxylic acid p-propyloxyphenyl ester,
- 7.0 wt. % of 2-(trans-4-pentylcyclohexyl)-1-(p-ethoxyphenyl)-ethane,
- 2.8 wt. % of 3-propyl-6-(trans-4-ethylcyclohexyl)pyridazine,
- 6.9 wt. % of 3-propyl-6-(trans-4-pentylcyclohexyl)pyridazine,
- 4.4 wt. % of 3-propyl-6-(trans-4-heptylcyclohexyl)pyridazine,
- 8.8 wt. % of 3-pentyl-6-(trans-4-pentylcyclohexyl)pyridazine,
- 10.0 wt. % of 4'-hexyl-4-biphenylcarboxylic acid 3-chloro-4-[(3-chloro-4-cyanophenoxy)carbonyl]phenyl ester,
- 10.0 wt. % of 4'-heptyl-4-biphenylcarboxylic acid 3-chloro-4-[(3 chloro 4-cyanophenoxy)carbonyl]phenyl ester;

m.p. (C-N) <0° C., cl.p. (N-I) 73° C.; $f_c$ (22° C.) = 3.4 kHz, $\Delta\epsilon_l$ (22° C.) = 8.24, $\Delta\epsilon_h$ (22° C.) = −4.48; $\eta$ (22° C.) = 73 cp.

Mixture Example 2
- 10.0 wt. % of trans-4-butylcyclohexanecarboxylic acid p-ethoxyphenyl ester,
- 14.0 wt. % of trans-4-butylcyclohexanecarboxylic acid p-pentyloxyphenyl ester,
- 9.0 wt. % of trans-4-pentylcyclohexanecarboxylic acid p-methoxyphenyl ester,
- 10.9 wt. % of trans-4-pentylcyclohexanecarboxylic acid p-propyloxyphenyl ester,
- 6.1 wt. % of 2-(trans-4-pentylcyclohexyl)-1-(p-ethoxyphenyl)ethane,
- 4.0 wt. % of 3-propyl-6-(trans-4-ethylcyclohexyl)pyridazine,
- 9.6 wt. % of 3-propyl-6-(trans-4-pentylcyclohexyl)pryidazine,
- 6.1 wt. % of 3-propyl-6-(trans-4-heptylcyclohexyl)pyridazine,
- 12.3 wt. % of 3-pentyl-6-(trans-4-pentylcyclohexyl)pyridazine,
- 6.0 wt. % of 4'-heptyl-4-biphenylcarboxylic acid 3-chloro-4-[(3-chloro-4-cyanophenoxy)carbonyl]phenyl ester,
- 6.0 wt. % of 4'-hexyl-4-biphenylcarboxylic acid 3-chloro-4-[(3-chloro-4-nitrophenoxy)carbonyl]phenyl ester,
- 6.0 wt. % of 4'-heptyl-4-biphenylcarboxylic acid 3-chloro-4-[(3-chloro-4-nitrophenoxy)carbonyl]phenyl ester;

m.p. (C-N) <0° C., cl.p. (N-I) 63° C.

Mixture Example 3
- 10.2 wt. % of trans-4-butylcyclohexanecarboxylic acid p-ethoxyphenyl ester,
- 14.3 wt. % of trans-4-butylcyclohexanecarboxylic acid p-pentyloxyphenyl ester,
- 9.2 wt. % of trans-4-pentylcyclohexanecarboxylic acid p-methoxyphenyl ester,
- 11.1 wt. % of trans-4-pentylcyclohexanecarboxylic acid p-propyloxyphenyl ester,
- 6.2 wt. % of 2-(trans-4-pentylcyclohexyl)-1-(p-ethoxyphenyl)-ethane,
- 9.1 wt. % of 4-pentyl-1-(trans-4-propylcyclohexyl)benzene,
- 2.6 wt. % of 3-propyl-6-(trans-4-ethylcyclohexyl)pyridazine
- 6.3 wt. % of 3-propyl-6-(trans-4-pentylcyclohexyl)pyridazine
- 4.0 wt. % of 3-propyl-6-(trans-4-heptylcyclohexyl)pyridazine
- 8.0 wt. % of 3-pentyl-6-(trans-4-pentylcyclohexyl)pyridazine
- 4.5 wt. % of 4'-heptyl-4-biphenylcarboxylic acid 3-chloro-4-[(p-cyanophenoxy)carbonyl]phenyl ester,
- 4.5 wt. % of p-[2-(trans-4-heptylcyclohexyl)ethyl]benzoic acid 3-chloro-4-[(p-cyanophenoxy)carbonyl]phenyl ester,
- 3.6 wt. % of p-[2-(trans-4-heptylcyclohexyl)ethyl]benzoic acid 3-chloro-4-[(p-(2,2-dicyano-1-methylvinyl)phenoxy)carbonyl]phenyl ester,
- 6.4 wt. % of 4'-heptyl-4-biphenylcarboxylic acid 3-chloro-4-[(3-chloro-4-cyanophenoxy)carbonyl]phenyl ester;

m.p (C-N) <0° C., cl.p. (N-I) 70° C.; $f_c$ (22° C.) = 3 kHz, $\Delta\epsilon_l$ (22° C.) = 4.39, $\Delta\epsilon_h$ (22° C.) = −4.0

Mixture Example 4
- 9.49 wt. % of trans-4-butylcyclohexanecarboxylic acid p-ethoxyphenyl ester,
- 13.36 wt. % of trans-4-butylcyclohexanecarboxylic acid p-pentyloxyphenyl ester,
- 8.58 wt. % of trans-4-pentylcyclohexanecarboxylic acid p-methoxyphenyl ester,
- 10.36 wt. % of trans-4-pentylcyclohexanecarboxylic acid p-propyloxyphenyl ester,
- 5.83 wt. % of 2-(trans-4-pentylcyclohexyl)-1-(p-ethoxyphenyl)ethane,
- 4.77 wt. % of 4-(trans-4-pentylcyclohexyl)-4'-[2-(trans-4-butylcyclohexyl)ethyl]biphenyl,
- 3.76 wt. % of 3-propyl-6-(trans-4-ethylcyclohexyl)pyridazine
- 9.15 wt. % of 3-propyl-6-(trans-4-pentylcyclohexyl)pyridazine
- 11.71 wt. % of 3-pentyl-6-(trans-4-pentylcyclohexyl)pyridazine
- 5.86 wt. % of 3-propyl-6-(trans-4-heptylcyclohexyl)pyridazine
- 5.71 wt. % of 4'-hexyl-4-biphenylcarboxylic acid 3-chloro-4-[(3-chloro-4-cyanophenoxy)carbonyl]phenyl ester,
- 5.71 wt. % of 4'-heptyl-4-biphenylcarboxylic acid 3-chloro-4-[(3-chloro-4-cyanophenoxy)carbonyl]phenyl ester,
- 5.71 wt. % of 4'-hexyl-4-biphenylcarboxylic acid 3-chloro-4-[(3-chloro-4-nitrophenoxy)carbonyl]phenyl ester;

m.p. (C-N) <−10° C., cl.p. (N-I) 73.7° C.; $f_c$ (22° C.,) = 3.5 kHz, $\Delta\epsilon_l$ (22° C.) = 5.22, $\Delta\epsilon_h$ (22° C.) = −5.2; $\eta$ (22° C.) = 67.4 cp.

Mixture Example 5
- 5.40 wt. % of trans-4-butylcyclohexanecarboxylic acid p-ethoxyphenyl ester,
- 4.95 wt. % of trans-4-pentylcyclohexanecarboxylic acid p-methoxyphenyl ester,
- 8.35 wt. % of trans-4-pentylcyclohexanecarboxylic acid p-propyloxyphenyl ester,
- 9.06 wt. % of trans-4-pentylcyclohexanecarboxylic acid trans-4-propylcyclohexyl ester,
- 13.42 wt. % of 2-(trans-4-pentylcyclohexyl)-1-(p-ethoxyphenyl)ethane,
- 6.45 wt. % of 1-[2-(trans-4-butylcyclohexyl)ethyl]-4-(trans-4-pentylcyclohexyl)benzene,
- 4.76 wt. % of 4-(trans-4-pentylcyclohexyl)-4'-[2-(trans-4-butylcyclohexyl)ethyl]biphenyl,
- 3.76 wt. % of 3-propyl-6-(trans-4-ethylcyclohexyl)pyridazine,
- 9.15 wt. % of 3-propyl-6-(trans-4-pentylcyclohexyl)pyridazine,
- 11.72 wt. % of 3-pentyl-6-(trans-4-pentylcyclohexyl)pyridazine,
- 5.85 wt. % of 3-propyl-6-(trans-4-heptylcyclohexyl)pyridazine,
- 5.71 wt. % of 4'-hexyl-4-biphenylcarboxylic acid 3-chloro-4-[(3-chloro-4-cyanophenoxy)carbonyl]phenyl
- 5.71 wt. % of 4'-hexyl-4-biphenylcarboxylic acid-3-chloro-4-[(3-chloro-4-nitrophenoxy)carbonyl]phenyl ester
- 5.71 wt. % of 4'-heptyl-4-biphenylcarboxylic acid-3-chloro-4-[(3-chloro-4-nitrophenoxy)carbonyl]phenyl ester;

m.p. (C-N) <−10° C., cl.p. (N-I) 70.1° C.; $f_c$ (22° C.) = 2.5 kHz, $\Delta\epsilon_l$ (22° C.) = 5.2, $\Delta\epsilon_h$ (22° C.) = −5.2; $\eta$ (22° C.) = 65 cp.

Mixture Example 6
- 8.48 wt. % of trans-4-butylcyclohexanecarboxylic acid p-ethoxyphenyl ester,
- 7.77 wt. % of trans-4-pentylcyclohexanecarboxylic acid p-methoxyphenyl ester,
- 13.11 wt. % of trans-4-pentylcyclohexanecarboxylic acid p-propyloxyphenyl ester,
- 14.22 wt. % of trans-4-pentylcyclohexanecarboxylic acid trans-4-propylcyclohexyl ester,
- 21.05 wt. % of 2-(trans-4-pentylcyclohexyl)-1-(p-ethoxyphenyl)ethane,
- 10.12 wt. % of 1-[2-(trans-4-butylcyclohexyl)ethyl]-4-(trans-4-pentylcyclohexyl)benzene,
- 2.91 wt. % of 4-(trans-4-pentylcyclohexyl)-4'-[2-(trans-4-butylcyclohexyl)ethyl]biphenyl,
- 0.60 wt. % of 3-propyl-6-(trans-4-ethylcyclohexyl)pyridazine,
- 1.46 wt. % of 3-propyl-6-(trans-4-pentylcyclohexyl)pyridazine,
- 1.86 wt. % of 3-pentyl-6-(trans-4-pentylcyclohexyl)pyridazine,
- 0.93 wt. % of 3-propyl-6-(trans-4-heptylcyclohexyl)pyridazine,
- 5.83 wt. % of 4'-hexyl-4-biphenylcarboxylic acid 3-chloro-4-[(3-chloro-4-cyanophenoxy)carbonyl]phenyl ester,
- 5.83 wt. % of 4'-hexyl-4-biphenylcarboxylic acid 3-chloro- -continued 4-[(3-chloro-4-nitrophenoxy)carbonyl]phenyl ester, 5.83 wt. % of 4'-heptyl-4-biphenylcarboxylic acid 3-chloro-4-[(3-chloro-4-nitrophenoxy)carbonyl]phenyl ester;

m.p. (C-N) < −10° C., cl.p. (N-I) 85.1° C.; $f_c$ (22° C.) = 2 kHz, $\Delta\epsilon_l$ (22° C.) = 5.2, $\Delta\epsilon_h$ (22° C.) = −2.2; $\eta$ (22° C.) = 55 cp.

Mixture Example 7

5.88 wt. % of trans-4-butylcyclohexanecarboxylic acid p-ethoxyphenyl ester, 5.39 wt. % of trans-4-pentylcyclohexanecarboxylic acid p-methoxyphenyl ester, 9.09 wt. % of trans-4-pentylcyclohexanecarboxylic acid p-propyloxyphenyl ester, 9.86 wt. % of trans-4-pentylcyclohexanecarboxylic acid trans-4-propylcyclohexyl ester, 14.61 wt. % of 2-(trans-4-pentylcyclohexyl)-1-(p-ethoxyphenyl)-ethane, 7.02 wt. % of 1-[2-(trans-4-butylcyclohexyl)ethyl]-4-(trans-4-pentylcyclohexyl)benzene, 7.41 wt. % of 4-(trans-4-pentylcyclohexyl)-4'-[2-(trans-4-butylcyclohexyl)ethyl]biphenyl, 3.66 wt. % of 3-propyl-6-(trans-4-ethylcyclohexyl)pyridazine 8.90 wt. % of 3-propyl-6-(trans-4-pentylcyclohexyl)pyridazine, 11.39 wt. % of 3-pentyl-6-(trans-4-pentylcyclohexyl)pyridazine, 5.69 wt. % of 3-propyl-6-(trans-4-heptylcyclohexyl)pyridazine, 3.70 wt. % of 4'-hexyl-4-biphenylcarboxylic acid 3-chloro 4-[(3-chloro-4-cyanophenoxy)carbonyl]phenyl ester, 3.70 wt. % of 4'-hexyl-4-biphenylcarboxylic acid 3-chloro-4-[(3-chloro-4-nitrophenoxy)carbonyl]phenyl ester, 3.70 wt. % of 4'-heptyl-4-biphenylcarboxylic acid 3-chloro-4-[(3-chloro-4-nitrophenoxy)carbonyl]phenyl ester;

m.p. (C-N) < −10° C., cl.p. (N-I) 70.0° C.; $f_c$ (22° C.) = 3 kHz, $\Delta\epsilon_l$ (22° C.) = 2.2, $\Delta\epsilon_h$ (22° C.) = −5.2; $\eta$ (22° C.) = 55 cp.

The following Examples illustrate the manufacture of the compounds of formula I and the preparation of the starting materials:

EXAMPLE 1

11.4 g of 2-chloro-4-[[p-(p-hexylphenyl)benzoyl]oxy]benzoic acid were heated to boiling for 2.5 hours with 5.35 g of thionyl chloride in 100 ml of benzene. The solvent and excess thionyl chloride were distilled off in vacuo and the residue was taken up twice in 50 ml of toluene each time and concentrated each time.

The crude 2-chloro-4-[[p-(p-hexylphenyl)benzoyl]oxy]benzoyl chloride obtained was dissolved in 125 ml of benzene and then added dropwise to a solution of 4.0 g of 3-chloro-4-cyanophenol in 100 ml of pyridine. The mixture was stirred at a bath temperature of 65° C. overnight, then poured into ice-cold, dilute hydrochloric acid and extracted with diethyl ether. The extract was washed several times with 3N hydrochloric acid, then washed neutral with water, dried and evaporated. The crude 4'-hexyl-4-biphenylcarboxylic acid 3-chloro-4-[(3-chloro-4-cyanophenoxy)carbonyl]phenyl ester obtained was chromatographed on silica gel with toluene/dichloromethane (1:1). The fractions (8.2 g) which were practically pure according to thin-layer chromatography were recrystallized once from ethyl acetate and once from ethyl acetate and a small amount of hexane; m.p. (C-N) 95° C., cl.p. (N-I) 235° C.

The 2-chloro-4-[[p-(p-hexylphenyl)benzoyl]oxy]benzoic acid used as the starting material was prepared as follows:

(a) 37.2 g of N,N'-dicyclohexylcarbodiimide were added portionwise within 10 minutes to a mixture of 45.2 g of 4'-hexyl-4-biphenylcarboxylic acid, 23.5 g of 2-chloro-4-hydroxybenzaldehyde and 1.5 g of 4-(dimethylamino)pyridine in 1500 ml of dichloromethane. The mixture was stirred at room temperature for 3 hours and then the precipitated N,N'-dicyclohexylurea was filtered off under suction. The filtrate was washed twice with 200 ml of 2N sodium hydroxide solution each time and four times with 200 ml of water each time, dried over sodium sulphate, filtered and concentrated.

(b) The crude 2-chloro-4-[[p-(p-hexylphenyl)benzoyl]oxy]benzaldehyde (67.1 g) obtained was dissolved in 2500 ml of acetone. 80 ml of Jones' reagent were added dropwise to this solution within 45 minutes, the mixture warming slightly. The mixture was stirred for a further 3 hours, then the precipitated inorganic material was filtered off under suction and the acetone was distilled off on a rotary evaporator. The residue was suspended in water and the suspension was suction filtered. The crude 2-chloro-4-[[p-(p-hexylphenyl)benzoyl]oxy]benzoic acid obtained was washed neutral on the suction filter with water and then, for purification, boiled up with methanol, cooled, filtered off and dried. Yield 58.5 g; m.p. 163.8°–165.5° C.

The following compounds were manufactured in an analogous manner:

4'-Heptyl-4-biphenylcarboxylic acid 3-chloro-4-[(3-chloro-4-cyanophenoxy)carbonyl]phenyl ester; m.p. (C-N) 95° C., cl.p. (N-I) 229° C.;

4'-heptyl-4-biphenylcarboxylic acid p-[(3-chloro-4-cyanophenoxy)carbonyl]phenyl ester; m.p. (C-N) 112° C., cl.p. (N-I) 289° C.;

4'-(pentyloxy)-4-biphenylcarboxylic acid 3-chloro-4-[(3-chloro-4-cyanophenoxy)carbonyl]phenyl ester; m.p. (C-N) 115.5° C., cl.p. (N-I) 272° C.;

4'-heptyl-4-biphenylcarboxylic acid 3-chloro-4-[(3,4-dicyanophenoxy)carbonyl]phenyl ester; m.p. (C-N) 146° C., cl.p. (N-I) 211.5° C.;

4'-heptyl-4-biphenylcarboxylic acid p-[(3,4-dicyanophenoxy)carbonyl]phenyl ester; m.p. (C-N) 162° C., cl.p. (N-I) 266.5° C.;

4'-pentyl-4-biphenylcarboxylic acid 3-chloro-4-[(4-nitrophenoxy)carbonyl]phenyl ester; m.p. (C-N) 124° C., cl.p. (N-I) >290° C.;

4'-heptyl-4-biphenylcarboxylic acid 3-chloro-4-[(4-nitrophenoxy)carbonyl]phenyl ester; m.p. (C-N) 96.5° C., cl.p. (N-I) >280° C.;

4'-hexyl-4-biphenylcarboxylic acid 3-chloro-4-[(3-chloro-4-nitrophenoxy)carbonyl]phenyl ester; m.p. (C-N) 94° C., cl.p. (N-I) 203° C.;

4'-heptyl-4-biphenylcarboxylic acid 3-chloro-4-[(3-chloro-4-nitrophenoxy)carbonyl]phenyl ester; m.p. (C-N) 102.5° C., cl.p. (N-I) 199.5° C.;

4'-hexyl-4-biphenylcarboxylic acid 3-chloro-4-[(3-methyl-4-cyanophenoxy)carbonyl]phenyl ester; m.p. (C-N) 110° C., cl.p. (N-I) 237° C.;

4'-heptyl-4-biphenylcarboxylic acid 3-chloro-4-[(3-methyl-4-cyanophenoxy)carbonyl]phenyl ester; m.p. (C-N) 101.5° C., cl.p. (N-I) 232° C.;

4'-hexyl-4-biphenylcarboxylic acid 3-chloro-4-[(3,4-dicyanophenoxy)carbonyl]phenyl ester; m.p. (C-N) 145° C., cl.p. (N-I) 219° C.

EXAMPLE 2

A suspension of 2.6 g of 4'''-pentyl-4-terphenyl-4'-carboxylic acid in 25 ml of thionyl chloride was heated to boiling for 2.5 hours. The thionyl chloride was subsequently distilled off and the residue was taken up twice in 50 ml of toluene each time and concentrated each time.

The crude 4''-pentyl-4-terphenyl-4'-carbonyl chloride obtained was dissolved in 50 ml of benzene and then added to a solution of 1.15 g of 3-chloro-4-cyanophenol in 30 ml of pyridine. The mixture was heated overnight with an oil-bath of 70° C. while stirring, then poured into ice-water and extracted with dichloromethane. The extract was washed several times with 3N hydrochloric acid, then washed with 2N sodium carbonate solution and with water, dried and evaporated. The crude 4''-pentyl-4-terphenyl-4'-carboxylic acid 3-chloro-4-cyanophenyl ester obtained was chromatographed on silica gel with toluene/dichloromethane (4:1). The fractions which were practically pure according to thin-layer chromatography were recrystallized twice from ethyl acetate: yield 2.3 g; m.p. (C-N) 161° C., cl.p. (N-I) 299° C.

EXAMPLE 3

In a manner analogous to that described in Example 1, from 2-chloro-4-[[p-(p-heptylphenyl)benzoyl]oxy]-benzoic acid and 3-chloro-4-(2,2-dicyanovinyl)phenol there was manufactured 4'-heptyl-4-biphenylcarboxylic acid 3-chloro-4-[(3-chloro-4-(2,2-dicyanovinyl)phenoxy)carbonyl]phenyl ester; m.p. (C-N) 120.5° C., cl.p. (N-I) 240.5° C.

The 3-chloro-4-(2,2-dicyanovinyl)phenol used as the starting material was prepared as follows:

A mixture of 3.2 g of 3-chloro-4-hydroxybenzaldehyde, 1.6 g of malononitrile, 0.31 g of ammonium acetate, 0.23 ml of glacial acetic acid and 100 ml of toluene was heated to boiling overnight on a water separator. The mixture was left to cool, the product precipitating partially. The precipitated product was brought into solution by dilution with diethyl ether. The mixture was then washed with saturated sodium chloride solution, dried over sodium sulphate, filtered and concentrated. The residue was dissolved in hot toluene and the solution was filtered. 3.2 g of 3-chloro-4-(2,2-dicyanovinyl)phenol of melting point 161°–162° C. crystallized from the filtrate.

EXAMPLE 4

Those compounds of formula I in which ring A signifies trans-1,4-cyclohexylene, $X^1$ signifies the ethylene group —$CH_2CH_2$— and ring B signifies p-phenylene can be manufactured in a manner analogous to that described in Example 1.

The carboxylic acids used as the starting materials can be prepared as illustrated hereinafter for p-[2-(trans-4-heptylcyclohexyl)ethyl]benzoic acid.

A solution of 21.3 g of p-[2-(trans-4-heptylcyclohexyl)ethyl]benzonitrile and 14.0 g of potassium hydroxide (85%) in 500 ml of ethylene glycol was heated to boiling for 8 hours (bath temperature 210° C.). After cooling, the mixture was poured into water and acidified with 3N hydrochloric acid. The precipitated p-[2-(trans-4-heptylcyclohexyl)ethyl]benzoic acid was filtered off under suction, washed on the suction filter with water and then taken up in diethyl ether. The solution was dried over sodium sulphate and evaporated. There were obtained 22.9 g of product which was pure according to thin-layer chromatography; m.p. 184°–187° C., cl.p. 220°–223° C.

EXAMPLE 5

Those compounds of formula I in which ring A signifies p-phenylene, $X^1$ signifies the ethylene group —$CH_2CH_2$—, ring B signifies trans-1,4-cyclohexylene and $X^2$ signifies the ester group —COO— can be manufactured in a manner analogous to that described in Example 1.

The trans-4-[2-(p-$R^1$-phenyl)ethyl]cyclohexanecarboxylic acids used as the starting materials can be prepared as illustrated hereinafter on the basis of the pentyl compound:

(a) A mixture of 2.51 g of (p-pentylphenyl)methyl-triphenylphosphonium bromide and 615 mg of 4-cyanocyclohexanecarboxaldehyde (cis/trans mixture about 1:1) in 30 ml of t-butyl methyl ether at 0° C. was placed in a sulphonation flask under argon gasification, treated within 2 minutes with 673 mg of solid potassium t-butylate and subsequently stirred at 0° C. for a further 1.5 hours. Then, the red-brown heterogeneous mixture was poured into 100 ml of water and extracted three times with 100 ml of diethyl ether each time. The organic phases were washed twice with 50 ml of water each time and once with 50 ml of saturated sodium chloride solution, dried over magnesium sulphate and concentrated. The residue was suspended in 150 ml of hexane, freed from precipitated triphenylphosphine oxide by filtration (rinsing with hexane) and the filtrate was concentrated. Low-pressure chromatography (0.4 bar) of the resulting oil (1.36 g) on silica gel with 3% ethyl acetate/petroleum ether as the eluant gave 1.02 g (81%) of 4-[2-(p-pentylphenyl)ethenyl]cyclohexanecarbonitrile as a colourless oil; Rf-values of this isomer mixture (10% ethyl acetate/petroleum ether): 0.27 and 0.36.

(b) 956 mg of the 4-[2-(p-pentylphenyl)ethenyl]cyclohexanecarbonitrile obtained were dissolved in 50 ml of toluene in a sulphonation flask, treated with 150 mg of palladium/carbon (10%) and hydrogenated at normal pressure and room temperature until the hydrogen uptake came to a standstill (about 30 minutes). Filtration of the mixture (rinsing with toluene), concentration of the filtrate and low-pressure chromatography (0.4 bar) of the residue (890 mg) on silica gel with 5% ethyl acetate/petroleum ether gave 788 mg (82%) of 4-[2-(p-pentylphenyl)ethyl]cyclohexanecarbonitrile as a viscous colourless oil. Although in the thin-layer chromatogram using different solvent systems as the eluant only a single spot appeared, according to gas chromatographic and NMR spectroscopic analysis this material was a cis/trans isomer mixture (about 1:3). Two-fold crystallization of this material from pentane at −20° C. finally yielded trans-4-[2-(p-pentylphenyl)ethyl]cyclohexanecarbonitrile of sufficient purity (according to gas chromatographic analysis 98.8% of trans compound and 1.2% of cis compound); m.p. 22.4° C., cl.p. (N-I) −14.1° C.

(c) A mixture of 567 mg of trans-4-[2-(p-pentylphenyl)ethyl]cyclohexanecarbonitrile and 20 ml of a 10:1 mixture of 2N potassium hydroxide solution and ethanol was heated to reflux for 2 hours under argon gasification in a round flask provided with a reflux condenser. The cooled mixture was diluted with 20 ml of water and extracted twice with 30 ml of diethyl ether each time. The separated aqueous phase was acidified with about 20 ml of 2N sulphuric acid and extracted three times with 50 ml of diethyl ether each time. The organic phases were washed twice with 50 ml of saturated sodium chloride solution each time, dried over magnesium sulphate and concentrated. There were obtained 490 mg (81%) of trans-4-[2-(p-pentylphenyl)ethyl]cyclohexanecarboxylic acid as colourless crystals which were purified further by recrystallization from hexane.

EXAMPLE 6

Those compounds of formula I in which rings A and B signify trans-1,4-cyclohexylene, $X^1$ signifies the ethylene group —$CH_2CH_2$— and $X^2$ signifies the ester group —COO— can be manufactured in a manner analogous to that described in Example 1.

The trans-4-[2-(trans-4-alkylcyclohexyl)ethyl]cyclohexanecarboxylic acids used as the starting materials can be prepared as illustrated hereinafter on the basis of the pentyl compound:

(a) 3.79 g of lithium aluminium hydride were placed in 100 ml of absolute tetrahydrofuran under argon gasification and treated within 30 minutes with a solution of 19.83 g of trans-4-pentylcyclohexanecarboxylic acid in 100 ml of absolute tetrahydrofuran. After completion of the addition, the mixture was heated to reflux for 1 hour, then cautiously added to 200 ml of 2N hydrochloric acid and extracted three times with 100 ml of diethyl ether each time. The organic phases were washed with 100 ml of saturated sodium carbonate solution, dried over potassium carbonate and concentrated. Distillation of the residue (19.2 g) gave in the main run 17.7 g (96%) of (trans-4-pentylcyclohexyl)methanol as a colourless oil (purity 99.9%); b.p. 89° C./0.2 mmHg.

(b) A solution of 3.69 g of (trans-4-pentylcyclohexyl)methanol and 5.51 g of triphenylphosphine in 70 ml of methylene chloride at −30° C. was placed under argon gasification and treated portionwise within 15 minutes with 7.30 g of solid tetrabromomethane so that the internal temperature did not exceed −20° C. After completion of the addition, the cooling bath was removed and the mixture was stirred for a further 18 hours with gradual warming to room temperature. The mixture was then concentrated on a rotary evaporator and the semi-crystalline residue obtained was triturated with 200 ml of warm hexane, filtered and the concentrated filtrate was chromatographed with hexane on a column of silica gel. There were obtained 4.79 g (97%) of trans-1-(bromomethyl)-4-pentylcyclohexane as a colourless liquid which was purified further by distillation; b.p. 82° C./0.08 mmHg.

(c) A mixture of 18.9 g of 1-methoxy-3-(trimethylsilyloxy)-1,3-butadiene [S. Danishefsky et al., J. Amer. Chem. Soc. 96, (1974) 7807], 6.4 g of acrylonitrile, 100 mg of dibenzoyl peroxide and 50 ml of benzene was heated to reflux for 23 hours under argon gasification. After cooling, the volatile constituents (benzene and excess acrylonitrile) were removed on a rotary evaporator and the residue was heated to reflux for 2 hours in 100 ml of tetrahydrofuran/1N hydrochloric acid (4:1). The cooled mixture was subsequently extracted three times with 100 ml of methylene chloride each time. The organic phases were washed twice with 100 ml of water each time and once with 100 ml of saturated sodium chloride solution, dried over magnesium sulphate and concentrated. There were obtained 10.3 g of a yellow oil which consisted of 87.9% of 4-cyano-3-cyclohexen-1-one, of 4.1% of 4-cyano-2-cyclohexen-1-one and of 2.7% of trans-4-cyano-3-methoxycyclohexanone (a hydrolysis product occurring as an intermediate). Bulb-tube distillation (130°–140° C./0.27-0.15 mmHg) of the oil obtained gave 7.64 g of a mixture of 4-cyano-3-cyclohexen-1-one and 4-cyano-2-cyclohexen-1-one as an orange crystallizing oil. This oil was dissolved in 70 ml of ethanol and hydrogenated in the presence of 764 mg of 10% palladium/carbon at normal pressure (hydrogen uptake 1425 ml). After filtration of the catalyst, washing with methylene chloride, concentration of the filtrate and bulb-tube distillation (130°–150° C./0.11 mmHg), there were obtained 5.45 g (70%) of 4-cyanocyclohexanone as a colourless oil; Rf-value [toluene/ethyl acetate (3:1)]: 0.25.

(d) 9.6 g of triphenyl(methoxymethyl)phosphonium chloride were suspended in 50 ml of t-butyl methyl ether under argon gasification and treated portionwise at −10° C. with 3.39 g of solid potassium t-butylate. After completion of the addition, the mixture was stirred at 0° to 5° C. for a further 30 minutes and then the deep orange, partially heterogeneous mixture was treated dropwise within 10 minutes with a solution of 2.30 g of 4-cyanocyclohexanone in 20 ml of t-butyl methyl ether. In so doing the internal temperature should not exceed 5° C. After completion of the addition, the now yellow-orange mixture was warmed to 25° C. and stirred for a further 2 hours. 50 ml of a 2% sodium hydrogen carbonate solution were subsequently added and the separated aqueous phase was extracted twice with 50 ml of diethyl ether each time. The organic phases were washed with 50 ml of saturated sodium chloride solution, dried over potassium carbonate and concentrated. The residual semi-crystalline orange oil was triturated with 400 ml of hexane, cooled to −20° C. and freed from precipitated triphenylphosphine oxide by filtration (rinsing with cold hexane). Low-pressure chromatography (0.4 bar) of the concentrated residue on silica gel using 10% ethyl acetate/petroleum ether as the eluant gave 1.60 g (56%) of 4-(methoxymethylene)cyclohexanecarbonitrile as a colourless oil (purity 97%).

(e) The 4-(methoxymethylene)cyclohexanecarbonitrile obtained was heated to reflux for 1.5 hours in 100 ml of tetrahydrofuran/0.2N hydrochloric acid (4:1). The cooled mixture was then poured into 50 ml of water and extracted three times with 50 ml of diethyl ether each time. The organic phases were washed with 50 ml of water and 50 ml of saturated sodium hydrogen carbonate solution, dried over magnesium sulphate and concentrated. There were obtained 1.35 g (94%) of a colourless oil which, according to gas chromatographic analysis, contained 92% of a mixture of the cis- and trans-4-cyanocyclohexanecarboxaldehydes (in the ratio of about 1:1). This material was used in the following reduction without additional purification. Rf-values [toluene/ethyl acetate(3:1)]: cis-4-cyanocyclohexanecarboxaldehyde 0.36, trans-4-cyanocyclohexanecarboxaldehyde 0.32.

(f) A solution of 1.34 g of 4-cyanocyclohexanecarboxaldehyde (cis/trans mixture) in 40 ml of 0.1N methanolic potassium hydroxide solution was treated portionwise at 0° C. under argon gasification with 378 mg of solid sodium borohydride. After completion of the addition, the mixture was stirred at 0° C. for a further 20 minutes, then 50 ml of water were added and the mixture was extracted three times with 50 ml of methylene chloride each time. The organic phases were washed twice with 50 ml of water each time, dried over magnesium sulphate and concentrated. Low-pressure chromatography (0.4 bar) of the residual oil on silica gel with chloroform/ethyl acetate (1:1) gave 1.22 g (90%) of 4-(hydroxymethyl)cyclohexanecarbonitrile (likewise as an about 1:1 mixture of the two epimers) as a colourless viscous oil. This material was used in the following tosylation without further purification. Rf-value of 4-(hydroxymethyl)cyclohexanecarbonitrile [chloroform-/ethyl acetate (1:1)]: 0.29 (longish spot).

(g) A solution of 1.20 g of the 4-(hydroxymethyl)cyclohexanecarbonitrile obtained in 5 ml of pyridine was treated portionwise at room temperature and under argon gasification with 2.46 g of p-tosyl chloride. After stirring at room temperature for 3.5 hours (formation of a white precipitate), the mixture, cooled to 0° C., was treated with about 2 ml of water, cautiously made acid with about 7 ml of concentrated hydrochloric acid and extracted three times with 30 ml of diethyl ether each time. The organic phases were washed with 50 ml of water and 50 ml of saturated sodium chloride solution, dried over magnesium sulphate and concentrated, 2.31 g of semi-crystalline oil remaining behind. Low-pressure chromatography (0.5 bar) on 480 g of silica gel using 30% ethyl acetate/petroleum ether as the eluant gave 1.06 g (42%) of trans-4-(tosyloxymethyl)cyclohexanecarbonitrile as a colourless cyrstallizing oil (m.p. 84°–85° C.) and 1.03 g (41%) of cis-4-(tosyloxymethyl)cyclohexanecarbonitrile as a colourless viscous oil. Rf-values (30% ethyl acetate/petroleum ether): trans product 0.25, cis product 0.20.

(h) 121 mg of magnesium shavings were covered with 3 ml of absolute tetrahydrofuran under argon gasification, treated with a crystal of iodine and then treated at reflux temperature with a solution of 989 mg of trans-1-(bromomethyl)-4-pentylcyclohexane [from paragraph (b)] in 7 ml of absolute tetrahydrofuran. After completion of the addition, the mixture was heated to reflux for a further 45 minutes.

The mixture, cooled to −78° C., was subsequently treated with 0.7 ml of a 0.1N solution of dilithium tetrachlorocuprate (prepared according to M. Tamura et al., Synthesis 1971, 303) in tetrahydrofuran and treated with a solution of 587 mg of trans-4-(tosyloxymethyl)-cyclohexanecarbonitrile in 9 ml of absolute tetrahydrofuran. The mixture, warmed to −15° C., was stirred for a further 21 hours, then treated with about 10 ml of saturated ammonium chloride solution and extracted three times with 50 ml of diethyl ether each time. The organic phases were washed with 50 ml of saturated sodium chloride solution, dried over magnesium sulphate and concentrated. Low-pressure chromatography (0.5 bar) of the residue on silica gel with 3% ethyl acetate/petroleum ether gave, besides a large amount of coupling product of trans-1-(bromomethyl)-4-pentylcyclohexane, 164 mg (28.5%) of trans-4-[2-(trans-4-pentylcyclohexyl)ethyl]cyclohexanecarbonitrile [353 mg of trans-4-(tosyloxymethyl)cyclohexanecarbonitrile could be recovered with 30% ethyl acetate/petroleum ether]. A single recrystallization from 5 ml of methanol yielded 96 mg of trans-4-[2-(trans-4-pentylcyclohexyl)ethyl]cyclohexanecarbonitrile as colourless crystals (purity 99.98%); solid-solid transition 39.3° C., m.p. 56.3° C., cl.p. 72.3° C. (nematic).

(i) The nitrile obtained can be saponified to trans-4-[2-(trans-4-pentylcyclohexyl)ethyl]cyclohexanecarboxylic acid in a manner analogous to that described in Example 5(c) with 2N potassium hydroxide solution and ethanol.

EXAMPLE 7

A mixture of 3 g of 2-chloro-4-[[(trans-4-heptylcyclohexyl)carbonyl]oxy]benzoic acid p-carboxyphenyl ester, 40 ml of benzene and 0.7 ml of thionyl chloride was heated to boiling for 2 hours. Benzene and excess thionyl chloride were distilled off in vacuo and the residue was taken up twice in 25 ml of toluene each time and concentrated each time.

The crude 2-chloro-4-[[(trans-4-heptylcyclohexyl)-carbonyl]oxy]benzoic acid p-(chlorocarbonyl)phenyl ester obtained was dissolved in 70 ml of benzene and then added dropwise to a solution of 1.04 g of 3-chloro-4-nitrophenol in 50 ml of pyridine. The reaction mixture was stirred overnight at a bath temperature of 65° C., then poured into ice-cold dilute hydrochloric acid and extracted with diethyl ether. The extract was washed four times with 50 ml of 3N hydrochloric acid each time and once with 50 ml of 2N sodium carbonate solution, washed neutral with water, dried and concentrated. The crude 2-chloro-4-[[(trans-4-heptylcyclohexyl)carbonyl]oxy]benzoic acid p-[(3-chloro-4-nitrophenoxy)-carbonyl]phenyl ester (3.2 g) obtained was chromatographed on silica gel with hexane/dioxan (volume ratio 3:1). The fractions which were pure according to thin-layer chromatography (1.8 g) were recrystallized twice from ethyl acetate; m.p. (C-N) 138° C., cl.p. (N-I) 237.5° C.

The 2-chloro-4-[[(trans-4-heptylcyclohexyl)carbonyl]oxy]benzoic acid p-carboxyphenyl ester used as the starting material was prepared as follows:

(a) A mixture of 20.61 g of 2-chloro-4-[[(trans-4-heptylcyclohexyl)carbonyl]oxy]benzoic acid [prepared in a manner analogous to that described in Example 1(a) and (b)], 70 ml of benzene and 8 ml of thionyl chloride was heated to boiling for 1.5 hours. Benzene and excess thionyl chloride were distilled off in vacuo and the residue was diluted twice with 20 ml of toluene each time and concentrated each time.

(b) The crude 2-chloro-4-[[(trans-4-heptylcyclohexyl)carbonyl]oxy]benzoyl chloride obtained was dissolved in 100 ml of benzene and then added dropwise to a solution of 6.61 g of p-hydroxybenzaldehyde in 110 ml of pyridine. The resulting suspension was stirred for 6 hours at a bath temperature of 65° C., then poured into ice-cold dilute hydrochloric acid and extracted with diethyl ether. The extract was washed in sequence twice with 100 ml of 3N hydrochloric acid each time, once with 200 ml of water, three times with 50 ml of ice-cold sodium hydroxide solution each time, once with 50 ml of saturated sodium hydrogen carbonate solution and once with 100 ml of water, dried and concentrated, there being obtained 19.1 g of crude product.

(c) The crude 2-chloro-4-[[(trans-4-heptylcyclohexyl)carbonyl]oxy]benzoic acid p-formylphenyl ester (19.1 g) obtained was dissolved in 800 ml of acetone. 30 ml of Jones' reagent were added dropwise to this solution within 15 minutes, the mixture warming slightly. The mixture was stirred for a further 40 minutes, then the separated inorganic material was filtered off under suction and the filtrate was concentrated. The residue was suspended in water and the suspension obtained was suction filtered. The residue was washed neutral with water on the suction filter and recrystallized from acetone, there being obtained 14.6 g of 2-chloro-4-[[(trans-4-heptylcyclohexyl)carbonyl]oxy]benzoic acid p-carboxyphenyl ester; m.p. (C-S) 135°–136° C., transition S-N 156° C., cl.p. (N-I) >300° C.

The following compounds were manufactured in an analogous manner:

2-Chloro-4-[[(trans-4-heptylcyclohexyl)carbonyl]oxy]-
   benzoic acid 3-chloro-4-[[(p-(2,2-dicyano-1-methylvinyl)phenoxy]carbonyl]phenyl ester; m.p. (C-N) 95.5° C., cl.p. (N-I) 233.5° C.;

2-chloro-4-[[(p-hexylphenyl)carbonyl]oxy]benzoic acid p-[(3-chloro-4-nitrophenoxy)carbonyl]phenyl ester; m.p. (C-S) 98° C., phase transitions S-S 104.5° C. and S-N 129.5° C., cl.p. (N-I) 235° C.;

2-chloro-4-[[(p-hexylphenyl)carbonyl]oxy]benzoic acid 3-chloro-4-[[(p-(2,2-dicyano-1-methylinyl)phenoxy]carbonyl]phenyl ester; m.p. (C-N) 154° C. or 160° C. (2 modifications), (N-I) 239° C.;

4-[[(p-hexylphenyl)carbonyl]oxy]benzoic acid 3-chloro-4-[(3-chloro-4-nitrophenoxy)carbonyl]phenyl ester; m.p. (C-N) 112° C., cl.p. (N-I) 255° C.;

2-chloro-4-[[(trans-4-heptylcyclohexyl)carbonyl]oxy]benzoic acid 3-chloro-4-[(3-chloro-4-cyanophenoxy)carbonyl]phenyl ester; m.p. 194° C.;

2-chloro-4-[[(trans-4-heptylcyclohexyl)carbonyl]oxy]benzoic acid 3-chloro-4-[(3-chloro-4-nitrophenoxy)carbonyl]phenyl ester; m.p. 198° C.;

4-[[(trans-4-heptylcyclohexyl)carbonyl]oxy]benzoic acid 3-chloro-4-[(3-chloro-4-nitrophenoxy)carbonyl]phenyl ester; m.p. (C-N) 158.5° C., cl.p. (N-I) 235.5° C.;

4-[[(p-hexylphenyl)carbonyl]oxy]benzoic acid 3-chloro-4-[(3-chloro-4-cyanophenoxy)carbonyl]phenyl ester; m.p. (C-N) 112° C., cl.p. (N-I) 251° C.;

4-[[(p-hexylphenyl)carbonyl]oxy]benzoic acid 3-chloro-4-[(3-methyl-4-nitrophenoxy)carbonyl]phenyl ester; m.p. (C-N) 127° C., cl.p. (N-I) 238° C.;

2-chloro-4-[[(p-hexylphenyl)carbonyl]oxy]benzoic acid 3-chloro-4-[(p-cyanophenoxy)carbonyl]phenyl ester; m.p. (C-N) 131° C., cl.p. (N-I) 258° C.;

4-[[(p-hexylphenyl)carbonyl]oxy]benzoic acid 3-chloro-4-[[(p-(2,2-dicyano-1-methylvinyl)phenoxy]carbonyl]phenyl ester; m.p. (C-N) 118° C., cl.p. (N-I) 276.5° C.;

2-chloro-4-[[(p-hexylphenyl)carbonyl]oxy]benzoic acid p-[[p-(2,2-dicyano-1-methylvinyl)phenoxy]carbonyl]phenyl ester; m.p. (C-N) 145.5° C., cl.p. (N-I) 276.5° C.

EXAMPLE 8

3.6 g of 4'-(trans-4-pentylcyclohexyl)-4-biphenylcarboxylic acid 4-carboxy-3-chlorophenyl ester were heated to boiling for 4 hours with 2.5 g of thionyl chloride in 150 ml of benzene. The solvent and excess thionyl chloride were then distilled off in vacuo and the residue was taken up twice in 50 ml of toluene each time and concentrated each time.

The crude 4'-(trans-4-pentylcyclohexyl)-4-biphenylcarboxylic acid 3-chloro-4-(chlorocarbonyl)phenyl ester obtained was dissolved in 150 ml of benzene and then added dropwise to a solution of 1.2 g of 3-chloro-4-nitrophenol in 110 ml of dry pyridine. The mixture was stirred at 65° C. overnight, then poured into a mixture of 500 ml of ice-water and 100 ml of concentrated hydrochloric acid and extracted with diethyl ether. The extract was washed three times with 100 ml of 3N hydrochloric acid each time and three times with 200 ml of water each time, then dried and evaporated. The crude 4'-(trans-4-pentylcyclohexyl)-4-biphenylcarboxylic acid 3-chloro-4-[(3-chloro-4-nitrophenoxy)carbonyl]phenyl ester obtained was chromatographed on silica gel with toluene/acetone (volume ratio 19:1). The fractions which were almost pure according to thin-layer chromatography (2.8 g) were recrystallized twice from ethyl acetate; m.p. (C-N) 132° C., cl.p. >250° C. (decomposition).

The 4'-(trans-4-pentylcyclohexyl)-4-biphenylcarboxylic acid 4-carboxy-3-chlorophenyl ester used as the starting material was prepared as follows:

(a) In a manner analogous to that described in Example 2, 7 g of 4'-(trans-4-pentylcyclohexyl)-4-biphenylcarboxylic acid were converted with thionyl chloride into the acid chloride and this was esterified with 3.1 g of 2-chloro-4-hydroxybenzaldehyde. There were thus obtained 7.7 g of crude 4'-(trans-4-pentylcyclohexyl)-4-biphenylcarboxylic acid 3-chloro-4-formylphenyl ester.

(b) The crude aldehyde obtained according to paragraph (a) was oxidized to the carboxylic acid in 1500 ml of acetone with Jones' reagent in a manner analogous to that described in Example 1, paragraph (b). The crude 4'-(trans-4-pentylcyclohexyl)-4-biphenylcarboxylic acid 4-carboxy-3-chlorophenyl ester obtained was washed with water and methanol on the suction filter, then dried and used without additional purification.

The following compounds were manufactured in an analogous manner:

4'-(Trans-4-pentylcyclohexyl)-4-biphenylcarboxylic acid 3-chloro-4-[(3-chloro-4-cyanophenoxy)carbonyl]phenyl ester; m.p. (C-N) 133° C., cl.p. (N-I) 361° C.;

4'-(trans-4-pentylcyclohexyl)-4-biphenylcarboxylic acid 3-chloro-4-[[(p-(2,2-dicyano-1-methylvinyl)phenoxy]carbonyl]phenyl ester; m.p. (C-N) 168.5° C., cl.p. (N-I) about 360° C.;

4''-pentyl-4-terphenylcarboxylic acid 3-chloro-4-[(3-chloro-4-cyanophenoxy)carbonyl]phenyl ester; m.p. (C-N) 167° C., cl.p. (N-I) 372° C.;

4''-pentyl-4-terphenylcarboxylic acid 3-chloro-4-[(3-chloro-4-nitrophenoxy)carbonyl]phenyl ester; m.p. (C-N) 177° C., cl.p. (N-I)>300° C.;

4''-hexyl-4-terphenylcarboxylic acid 3-chloro-4-[(3-chloro-4-cyanophenoxy)carbonyl]phenyl ester; m.p. (C-N) 151.5° C., cl.p. (N-I) 355° C.;

4''-hexyl-4-terphenylcarboxylic acid 3-chloro-4-[(3-chloro-4-nitrophenoxy)carbonyl]phenyl ester; m.p. (C-N) 162.5° C., cl.p. (N-I)>270° C.

4'-[2-(trans-4-heptylcyclohexyl)ethyl]-4-biphenylcarboxylic acid 3-chloro-4-[(3-chloro-4-nitrophenoxy)carbonyl]phenyl ester; m.p. (C-N) 127° C., cl.p. (N-I)>250° C.;

4'-[2-(trans-4-heptylcyclohexyl)ethyl]-4-biphenylcarboxylic acid 3-chloro-4-[(3-chloro-4-cyanophenoxy)carbonyl]phenyl ester; m.p. (C-N) 116° C., (N-I) 300° C.;

4'''-[2-(trans-4-heptylcyclohexyl)ethyl]-4-biphenylcarboxylic acid 3-chloro-4-[[p-(2,2-dicyano-1-methylvinyl)phenoxy]carbonyl]phenyl ester; m.p. (C-N) 141° C., cl.p. (N-I) 320° C.;

4-[4-(trans-4-heptylcyclohexyl)benzoyloxy]benzoic acid 3-chloro-4-[(3-chloro-4-nitrophenoxy)carbonyl]phenyl ester; m.p. (C-N) 155° C., cl.p. (N-I)>250° C.;

4-[4-(trans-4-heptylcyclohexyl)benzoyloxy]benzoic acid 3-chloro-4-[(3-chloro-4-cyanophenoxy)carbonyl]phenyl ester; m.p. (C-N) 144,5° C., cl.p. (N-I) 380° C.

We claim:

1. A compound of the formula:

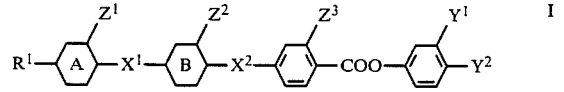

wherein $X^2$ is —COO—; $X^1$ is p—$C_6H_4$—, p—$C_6H_4$—$CH_2CH_2$—, —$CH_2CH_2$—p—$C_6H_4$—, p—$C_6H_4$—COO— or —COO—p—$C_6H_4$—; ring A is a benzene ring or trans-1,4-cyclohexylene; ring B is a benzene ring; $Z^1$ and $Z^2$ individually are hydrogen or when positioned on a benzene ring which is not linked directly with a further ring via a single covalent bond, $Z^1$ and $Z^2$ also can be halogen, cyano or methyl; $Z^3$ is hydrogen, halogen, cyano or methyl; $Y^2$ is cyano, nitro, 2,2-dicyanovinyl or when $Y^1$ is hydrogen $Y^2$ also can be 2,2-dicyano-1-methylvinyl; $Y^1$ is halogen, cyano, $C_1$–$C_3$-alkyl or hydrogen; and $R^1$ is $C_1$–$C_{12}$-alkyl or when positioned on a benzene ring $R^1$ also can be $C_1$–$C_{12}$-alkoxy.

2. A compound of claim 1 wherein $X^1$ is p-phenylene; and $Y^1$ is halogen, cyano, $C_1$–$C_3$-alkyl or hydrogen.

3. The compound of claim 1 wherein $Z^1$, $Z^2$ and $Z^3$ are hydrogen or at most two of $Z^1$, $Z^2$ and $Z^3$ are chlorine and the remainder are hydrogen.

4. The compound of claim 3 wherein $Y^1$ is hydrogen, fluorine, chlorine, cyano or methyl.

5. The compound of claim 1 having the formula:

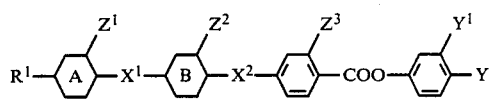

II in which $X^2$ is —COO—; $Y^2$ is cyano, nitro, 2,2-dicyanovinyl or when $Y^1$ is hydrogen $Y^2$ also can be 2,2-dicyano-1-methylvinyl; $X^1$ is p—$C_6H_4$—, p—$C_6H_4$—$CH_2CH_2$—, —$CH_2CH_2$—p—$C_6H_4$—, p—$C_6H_4$—COO— or —COO—p—$C_6H_4$—; ring A is p-phenylene or trans-1,4-cyclohexylene; $Z^2$ is hydrogen; $Z^3$ is hydrogen or chlorine; $Y^1$ is fluorine, chlorine, cyano, methyl or hydrogen; and $R^1$ is $C_1$–$C_{12}$-alkyl or when positioned on a benzene ring $R^1$ also can be $C_1$–$C_{12}$-alkoxy.

6. The compound of claim 5 wherein $X^1$ is p-phenylene.

7. The compound of claim 5 wherein $Y^1$ is chlorine, cyano, or hydrogen.

8. The compound of claim 5 wherein $Y^2$ is cyano or nitro.

9. The compound of claim 8 wherein $Y^1$ is chlorine.

10. The compound of claim 5 wherein $Y^1$ is hydrogen and $Y^2$ is 2,2-dicyano-1-methylvinyl.

11. The compound of claim 5 wherein ring A is trans-1,4-cyclohexylene.

12. The compound of claim 5 wherein $R^1$ is a straight-chain alkyl group of 1 to 12 carbon atoms.

13. The compound of claim 5 wherein the alkyl or alkoxy group of $R^1$ contains 3 to 10 carbon atoms.

14. The compound of claim 13 wherein the alkyl or alkoxy group of $R^1$ contains 5 to 9 carbon atoms.

15. The compound of claim 5 wherein $X^1$ is p-phenylene; ring A is trans-1,4-cyclohexylene; $Z^2$ is hydrogen; $Y^2$ is cyano or nitro; and $Z^3$ is hydrogen or chlorine.

16. A liquid crystalline mixture comprising at least two components wherein at least one of the components is a compound of the formula:

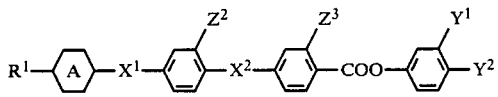

I wherein $X^2$ is —COO—; $X^1$ is p—$C_6H_4$—, p—$C_6H_4$—$CH_2CH_2$—, —$CH_2CH_2$—p—$C_6H_4$—, p—$C_6H_4$—COO— or —COO—p—$C_6H_4$—; ring A is a benzene ring or trans-1,4-cyclohexylene; ring B is a benzene ring; $Z^1$ and $Z^2$ individually are hydrogen or when positioned on a benzene ring which is not linked directly with a further ring via a single covalent bond, $Z^1$ and $Z^2$ also can be halogen, cyano or methyl; $Z^3$ is hydrogen, halogen, cyano or methyl; $Y^2$ is cyano, nitro, 2,2-dicyanovinyl or when $Y^1$ is hydrogen $Y^2$ also can be 2,2-dicyano-1-methylvinyl; $Y^1$ is halogen, cyano, $C_1$–$C_3$-alkyl or hydrogen; and $R^1$ is $C_1$–$C_{12}$-alkyl or when positioned on a benzene ring $R^1$ also can be $C_1$–$C_{12}$-alkoxy.

17. The liquid crystalline mixture of claim 16 comprising three components A, B and C, each of which contains one or more compounds, wherein component A has a viscosity of at most about 40 cp, a clearing point of at least about 40° C. and a dielectric anisotropy between about −2 and about +1, component B has a dielectric anisotropy below about −2, component C has a dielectric anisotropy above about +10, a clearing point of at least about 100° C. and a cross-over frequency in the total mixture of at most about 15 kHz at 20° C., and wherein component C contains at least one compound of formula I.

18. The liquid crystalline mixture of claim 17 comprising at least about 30 wt.% of component A, about 3–50 wt.% of component B and about 5–40 wt.% of component C.

19. An electro-optical cell comprising:
(a) two plate means;
(b) liquid crystal means disposed between the two plate means and including a compound of the formula:

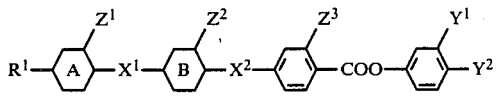

I wherein $X^2$ is —COO—; $X^1$ is p—$C_6H_4$—, p—$C_6H_4$—$CH_2CH_2$—, —$CH_2CH_2$—p—$C_6H_4$—, p—$C_6H_4$—COO— or —COO—p—$C_6H_4$—; ring A is a benzene ring or trans-1,4-cyclohexylene; ring B is a benzene ring; $Z^1$ and $Z^2$ individually are hydrogen or when positioned on a benzene ring which is not linked directly with a further ring via a single covalent bond, $Z^1$ and $Z^2$ also can be halogen, cyano or methyl; $Z^3$ is hydrogen, halogen, cyano or methyl; $Y^2$ is cyano, nitro, 2,2-dicyanovinyl or when $Y^1$ is hydrogen $Y^2$ also can be 2,2-dicyano-1-methylvinyl; $Y^1$ is halogen, cyano, $C_1$–$C_3$-alkyl or is hydrogen; and $R^1$ is $C_1$–$C_{12}$-alkyl or when positioned on a benzene ring $R^1$ also can be $C_1$–$C_{12}$-alkoxy; and
(c) means for applying an electrical potential to said plate means.

20. The compound of claim 1, 4'-(trans-4-pentylcyclohexyl)-4-biphenylcarboxylic acid 3-chloro-4-[(3-chloro-4-nitrophenoxy)carbonyl]phenyl ester.

21. The compound of claim 1, 4'-(trans-4-pentylcyclohexyl)-4-biphenylcarboxylic acid 3-chloro-4-[(3-chloro-4-cyanophenoxy)carbonyl]phenyl ester.

22. The compound of claim 1, 4'-(trans-4-pentylcyclohexyl)-4-biphenylcarboxylic acid 3-chloro-4-[[(p-2,2-dicyano-1-methylvinyl)phenoxyl]carbonyl]phenyl ester.

23. The compound of claim 1, 4'-[2-(trans-4-heptylcyclohexyl)ethyl]-4-biphenylcarboxylic acid 3-chloro-4-[(3-chloro-4-nitrophenoxy)carbonyl]phenyl ester.

24. The compound of claim 1, 4'-[2-(trans-4-heptylcyclohexyl)ethyl]-4-biphenylcarboxylic acid 3-chloro-4-[(3-chloro-4-cyanophenoxy)carbonyl]phenyl ester.

25. The compound of claim 1, 4'-[2-(trans-4-heptylcyclohexyl)ethyl]-3-biphenylcarboxylic acid 3-chloro-4-[[p-(2,2-dicyano-1-methylvinyl)phenoxy]carbonyl]phenyl ester.

* * * * *